(12) United States Patent
Maurer et al.

(10) Patent No.: US 10,286,137 B2
(45) Date of Patent: May 14, 2019

(54) OXYGENATOR MODULE, OXYGENATOR AND PRODUCTION METHOD

(71) Applicant: Novalung GmbH, Heilbronn (DE)

(72) Inventors: Andreas Maurer, Tübingen (DE); Josef Bogenschuetz, Bisingen (DE); Thomas Schmitz-Rode, Aachen (DE); Ulrich Steinseifer, Hauset (BE); Jutta Arens, Aachen (DE); Georg Wagner, Niederzissen (DE); Ralf Borchardt, Aachen (DE); Peter Christian Schlanstein, Aachen (DE)

(73) Assignee: Novalung GmbH, Heilbronn (DE)

( * ) Notice: Subject to any disclaimer, the term of this patent is extended or adjusted under 35 U.S.C. 154(b) by 471 days.

(21) Appl. No.: 14/889,751

(22) PCT Filed: May 8, 2014

(86) PCT No.: PCT/EP2014/001245
§ 371 (c)(1),
(2) Date: Nov. 6, 2015

(87) PCT Pub. No.: WO2014/183852
PCT Pub. Date: Nov. 20, 2014

(65) Prior Publication Data
US 2016/0095969 A1    Apr. 7, 2016

(30) Foreign Application Priority Data

May 17, 2013  (EP) ..................................... 13002624

(51) Int. Cl.
*A61M 1/16* (2006.01)
*B01D 63/02* (2006.01)
(Continued)

(52) U.S. Cl.
CPC ........ *A61M 1/1698* (2013.01); *A61M 1/1623* (2014.02); *A61M 1/262* (2014.02);
(Continued)

(58) Field of Classification Search
CPC .. A61M 1/1698; A61M 1/1623; A61M 1/262; A61M 1/32; A61M 2207/00;
(Continued)

(56) References Cited

U.S. PATENT DOCUMENTS 5,162,101 A * 11/1992 Cosentino ........... A61M 1/1698
128/DIG. 3
6,117,390 A * 9/2000 Corey, Jr. ........... A61M 1/1698
422/44
(Continued)

FOREIGN PATENT DOCUMENTS

CN        101121099 B    6/2010
CN        202459508 U   10/2012
(Continued)

*Primary Examiner* — Philip R Wiest
(74) *Attorney, Agent, or Firm* — Seed Intellectual Property Law Group LLP

(57) ABSTRACT

An oxygenator module for gas exchange between blood and a gas in an extracorporeal lung support system, with several layers of semipermeable, gas-perfusable hollow fibers, wherein the hollow fibers of one of the layers are oriented at an angle of rotation about a central longitudinal axis of the oxygenator module with respect to the hollow fibers of another one of the layers, and with a potting which extends along the central longitudinal axis and in which the hollow fibers are fixed, wherein the potting defines a cavity that extends along the central longitudinal axis and in which the hollow fibers are arranged and which is blood-perfusable in the direction of the central longitudinal axis, wherein the potting has an essentially circular inner sheath surface that
(Continued)

limits the cavity radially outward; as well as a method for producing the oxygenator module.

17 Claims, 17 Drawing Sheets

(51) Int. Cl.
  *B01D 65/08* (2006.01)
  *B29C 41/04* (2006.01)
  *B29C 41/20* (2006.01)
  *A61M 1/26* (2006.01)
  B29K 75/00 (2006.01)
  B29K 623/00 (2006.01)
  B29L 31/00 (2006.01)

(52) U.S. Cl.
  CPC ......... *B01D 63/021* (2013.01); *B01D 63/026* (2013.01); *B01D 65/08* (2013.01); *B29C 41/04* (2013.01); *B29C 41/20* (2013.01); *A61M 2207/00* (2013.01); *B01D 2313/10* (2013.01); *B01D 2321/2016* (2013.01); *B01D 2321/2025* (2013.01); *B29K 2075/00* (2013.01); *B29K 2623/00* (2013.01); *B29K 2623/10* (2013.01); *B29L 2031/7546* (2013.01)

(58) Field of Classification Search
  CPC .... B01D 63/021; B01D 63/026; B01D 63/08; B01D 2313/10; B01D 2321/2016; B01D 2321/2025; B29C 41/04; B29C 41/20
  See application file for complete search history.

(56) References Cited

U.S. PATENT DOCUMENTS

| | | |
|---|---|---|
| 2012/0190103 A1 | 7/2012 | Maurer |
| 2012/0193289 A1* | 8/2012 | Cloutier ............ A61M 1/1698 |
| | | 210/646 |
| 2012/0321512 A1 | 12/2012 | Kawamura et al. |
| 2013/0043177 A1 | 2/2013 | Taylor et al. |
| 2015/0314059 A1* | 11/2015 | Federspiel .......... A61M 1/1698 |
| | | 600/16 |
| 2018/0117231 A1 | 5/2018 | Matheis et al. |

FOREIGN PATENT DOCUMENTS

| | | |
|---|---|---|
| DE | 43 08 850 A1 | 9/1994 |
| EP | 0 376 298 A1 | 7/1990 |
| EP | 0 521 495 A2 | 1/1993 |
| EP | 1 864 709 A2 | 12/2007 |
| GB | 1 480 406 A | 7/1977 |
| JP | 4-193178 A | 7/1992 |
| JP | 2008-30023 A | 2/2008 |
| JP | 2009-509351 A | 3/2009 |
| JP | 2009-082695 A | 4/2009 |
| WO | 2009/110652 A1 | 9/2009 |
| WO | 2009/155248 A1 | 12/2009 |
| WO | 2014/183852 A1 | 11/2014 |
| WO | 2018/085620 A1 | 5/2018 |

* cited by examiner

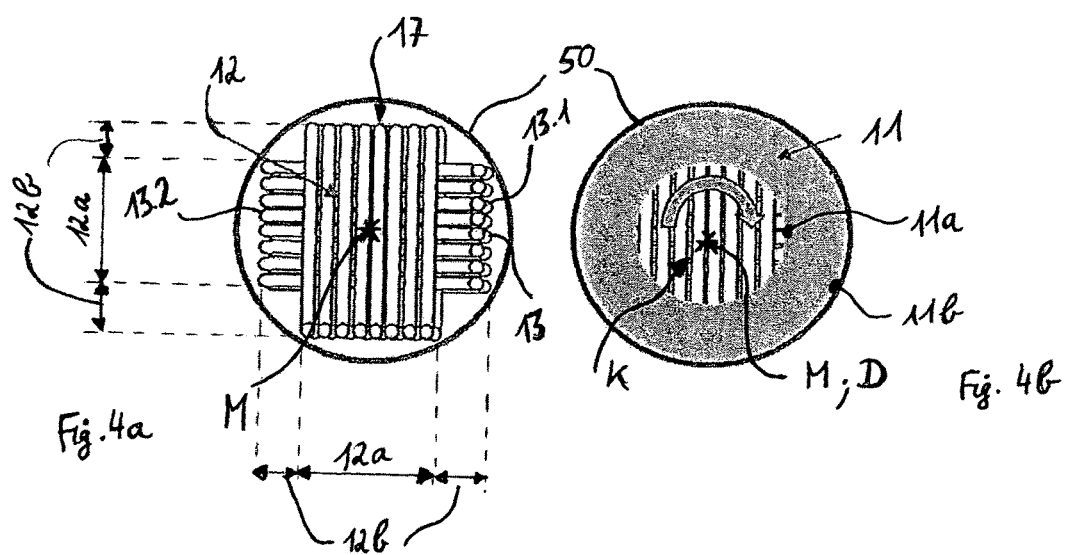

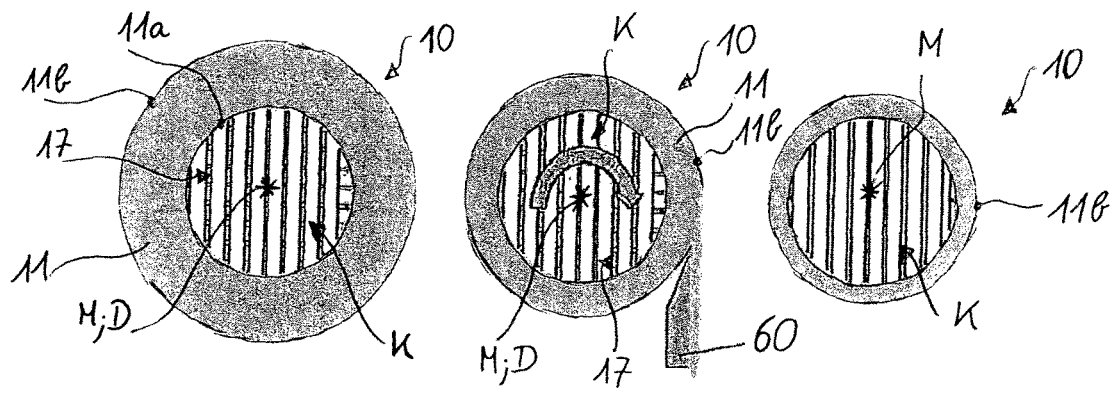
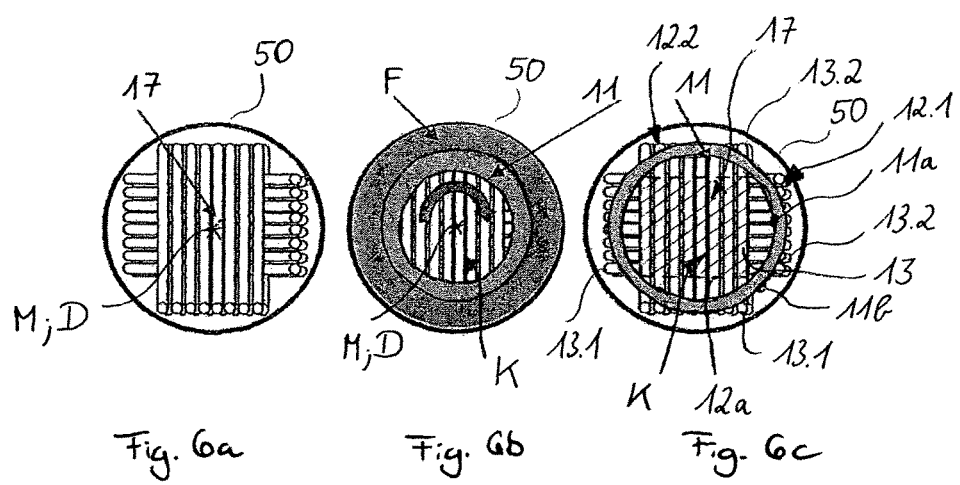

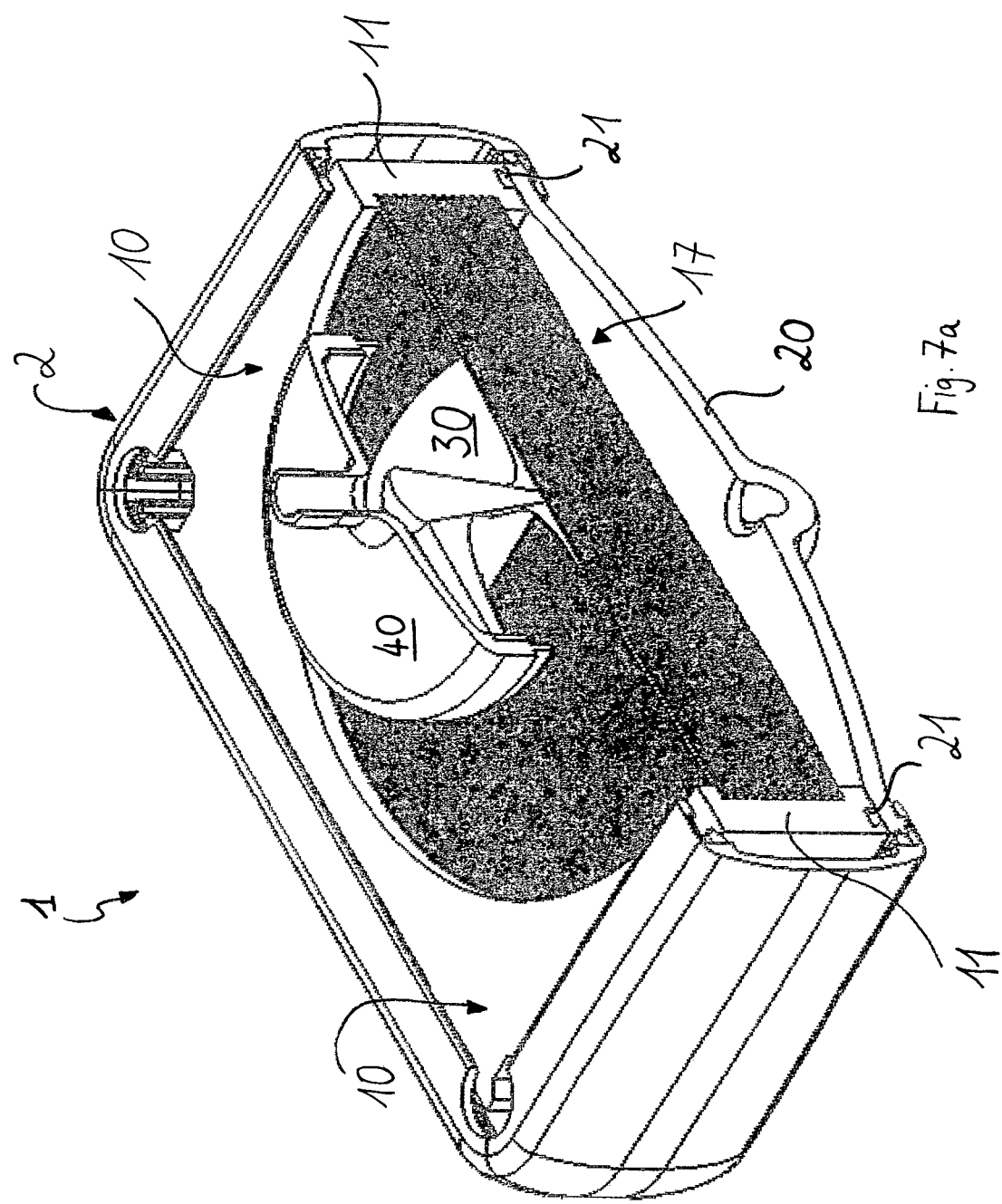

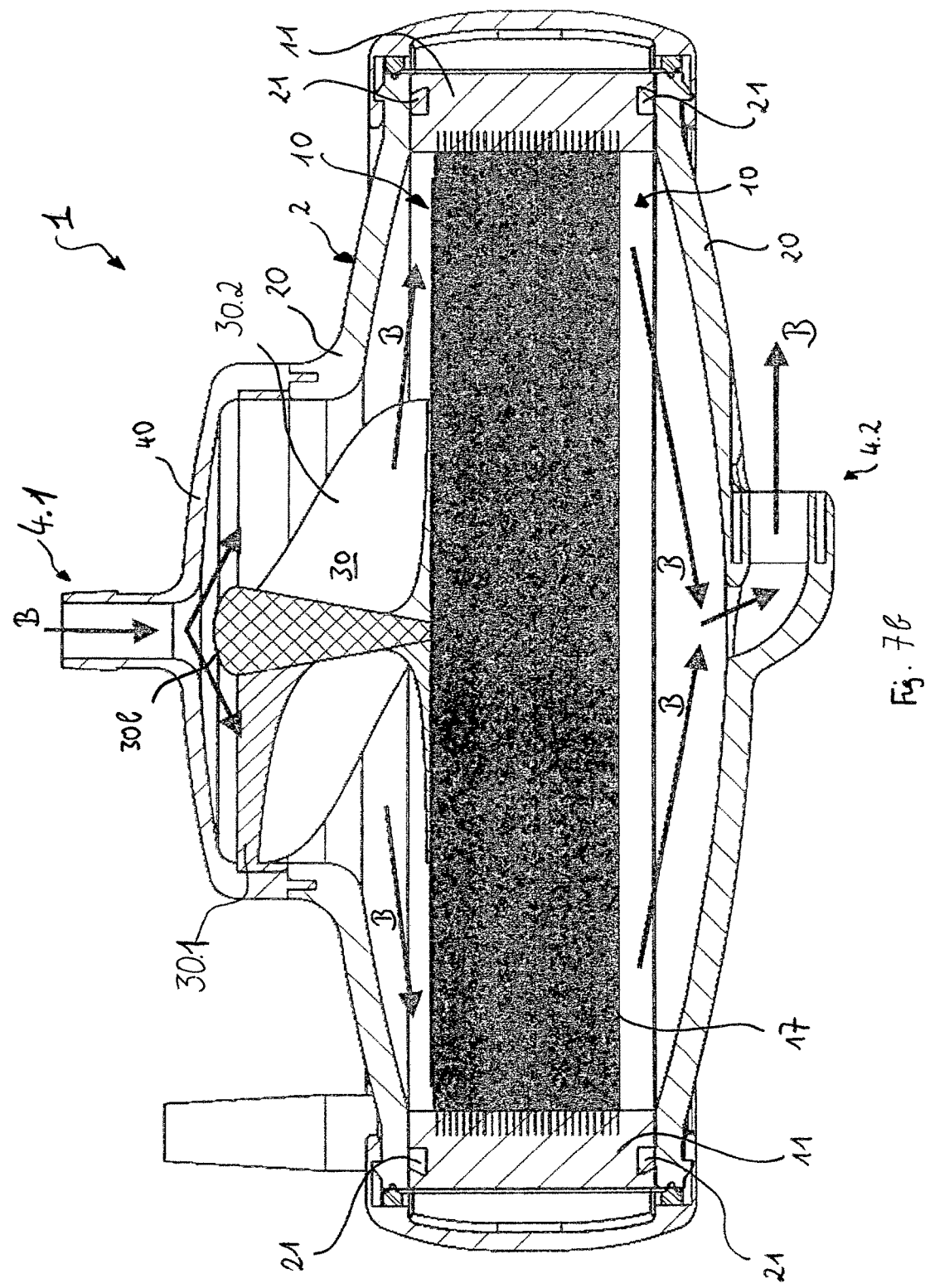

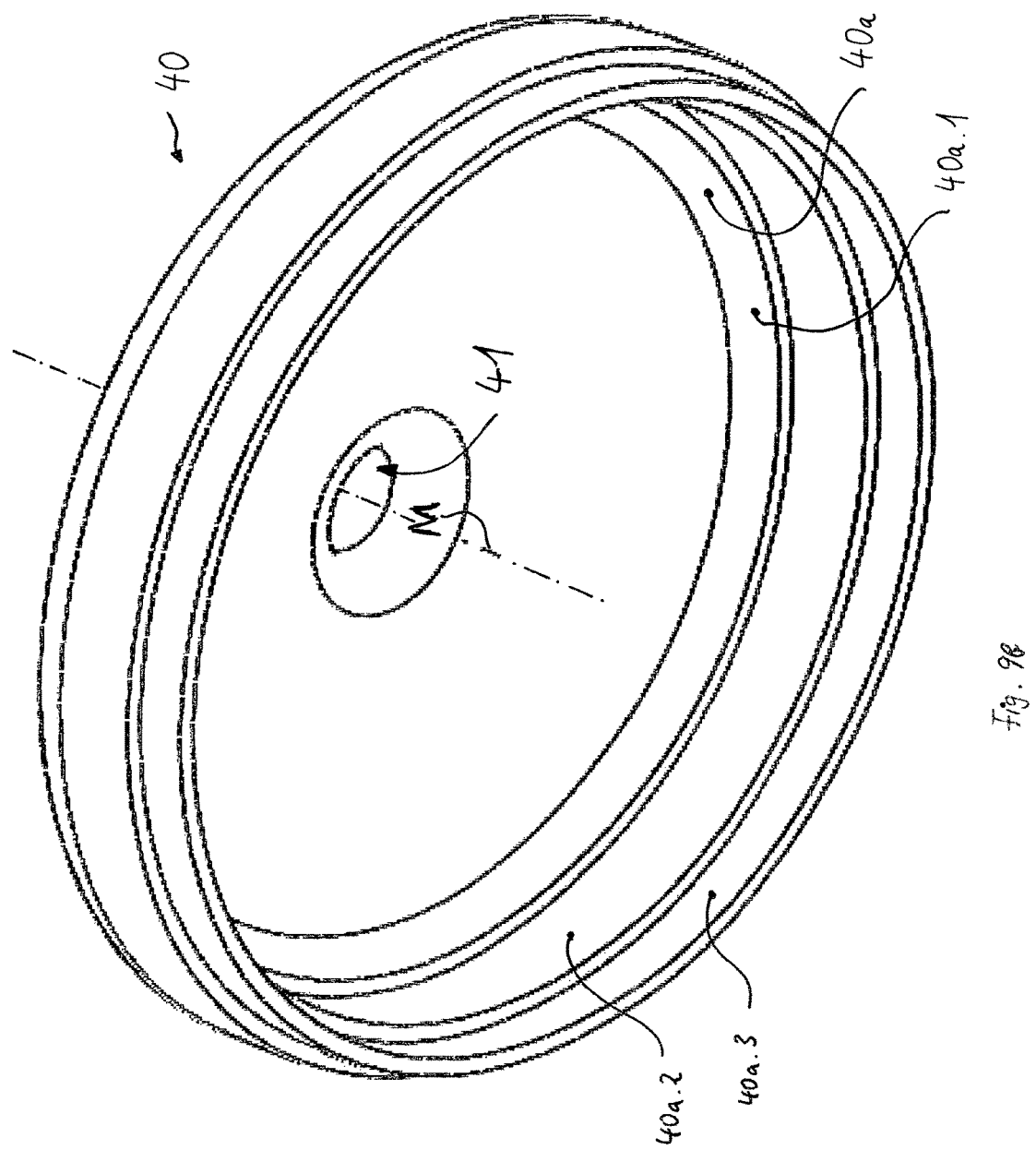

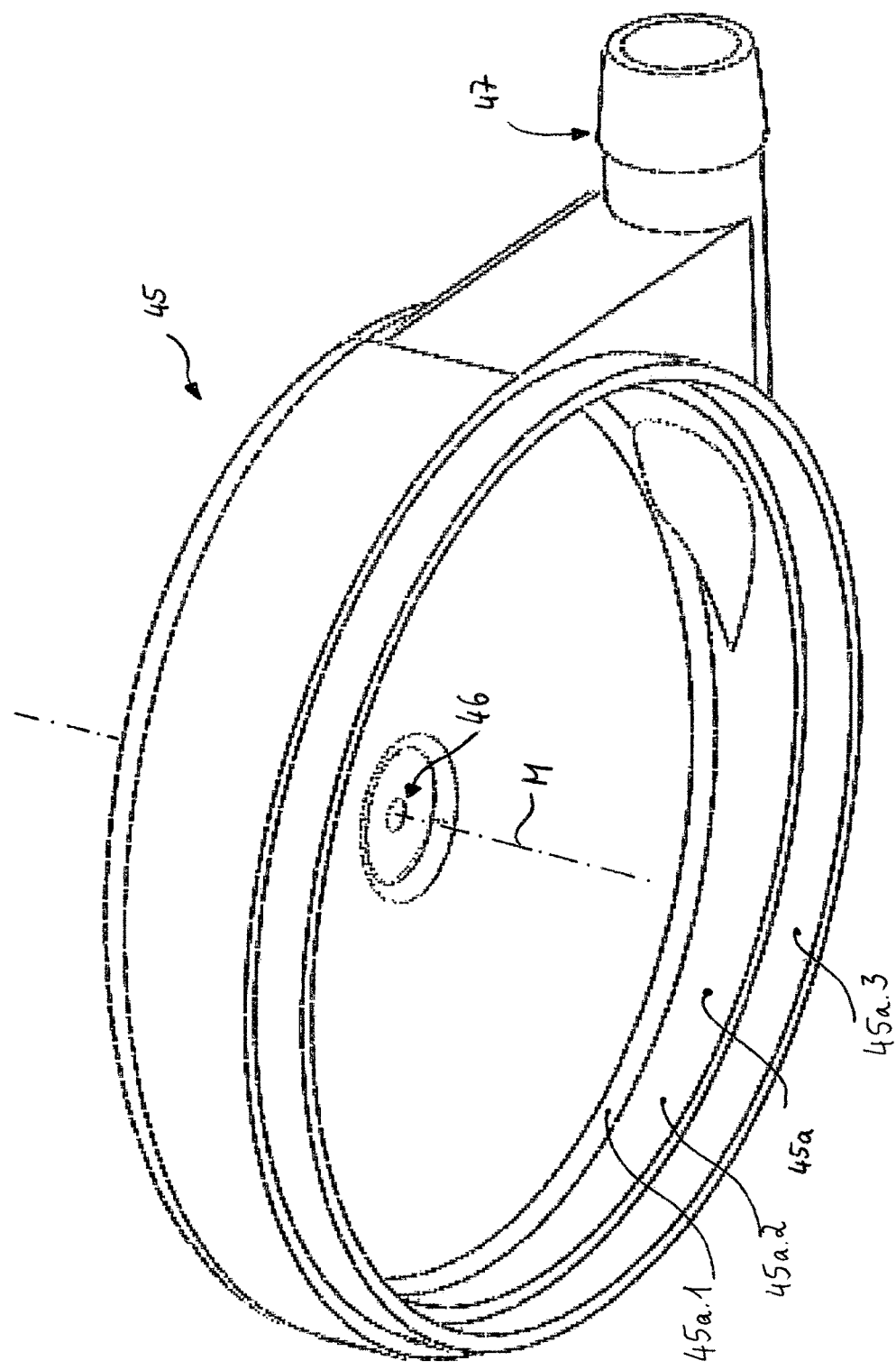

OXYGENATOR MODULE, OXYGENATOR AND PRODUCTION METHOD

BACKGROUND

Technical Field

The present invention relates to an oxygenator module according to the preamble of claim 1 as well as an oxygenator according to the preamble of the coordinate apparatus claim as well as a production method according to the preamble of the coordinate method claim.

Description of the Related Art

Blood-gas exchangers or artificial lungs that are to replace or at least support the natural lung function temporarily or even long-term are referred to as oxygenators. Oxygenators are also used, for example, in the field of cardiac surgery as part of a heart-lung machine. A special field of application is the at least short-term treatment of acute lung failure. Oxygenators are used for patients, for example, who are treated, especially in an intensive care unit, with so-called extracorporeal membrane oxygenation (ECMO) to support the heart and/or the lungs. The most common type of oxygenator is the membrane oxygenator. Oxygenators are, for example, used for the delivery of oxygen to the blood and the absorption of carbon dioxide from the blood. For this purpose, an oxygen-rich gas, for example, can be guided through semipermeable, only gas-perfusable hollow fiber membranes around which blood flows. Similarly to the natural lung, the gas exchange in this process is based on diffusion, in particular due to a difference in concentration (a partial pressure difference) of oxygen or carbon dioxide in the blood and in the gas.

The hollow fiber membranes consist, for example, of a plurality of hollow fibers from microporous plastics, for example polypropylene or polymethylpentene, that are arranged in layers (in particular fiber mats). The individual hollow fibers have a length of 100 to 200 mm, for example, and are arranged at a distance of 0.1-0.2 mm, for instance. They can be connected with each another or knotted together by so-called warp threads. The fiber mats formed by a plurality of hollow fibers can be designed to be one or two layers. Plasma-tight hollow fibers with a closed outer layer (closed porous fibers, in particular polymethylpentene-based (PMP) fibers) or non-plasma-tight hollow fibers with a non-closed outer layer (continuously porous fibers, in particular polypropylene-based fibers) can be provided. Furthermore, a distinction is made between plasma-tight (in particular polypropylene-based) and highly porous, non-plasma-tight (in particular polymethylpentene-based) fibers. Plasma-tight fibers are preferably used for oxygenators that must be used for a longer period of time of, for example, 14 days, in particular up to 29 days, particularly for the ECMO. The hollow fibers are arranged in an oxygenator module of the oxygenator.

Disadvantageous in this respect is in particular in connection with extracorporeal lung support systems that the oxygenators mostly cannot be used for longer than a period of one month, particularly due to the risk of coagulation (so-called "clotting"), which reduces the gas exchange capacity. This risk exists primarily with low blood flows and/or oxygenators that are not uniformly passed through in consequence of their geometry. Low blood flows lie, for example, in the range of 0.5-1.5 L/min or below. The oxygenators are also no longer passed through uniformly, i.e., no longer with uniform flow rate, particularly with increased operating time, as coagulations form. Often, areas develop that are passed through only with lower than the optimum flow rate. This disadvantageously affects primarily the gas exchange capacity for oxygen (O2), whereas the gas exchange capacity for carbon dioxide (CO2) depends more on the gas flow than on the blood flow. Here, the risk of coagulation exists across areas in which blood stagnation or blood stasis occurs.

In order for the perfusion with blood to take place as uniformly as possible, it is known to arrange a blood distributor plate upstream of the hollow fibers in a housing of the oxygenator. The distributor plates have the task of areally spreading the blood flow. They can be designed, for example, as perforated, transparent plates that do not have any openings in the area of the incident blood stream. Furthermore, a cover of the housing can have a flow-guiding geometry in a blood inlet area and can define, especially with an angular housing, an inclined plane for compensating pressure differences. Here, distributor legs are also provided, by means of which an inflow can be adjusted, even though the inflow mostly does not occur in a uniform manner in this process.

Even the specific arrangement of the fibers in the oxygenator module can influence the gas exchange rate. Oxygenator modules are known in which the individual layers of hollow fibers are arranged one above the other and at the same time, the fibers in one of the layers are turned with respect to the fibers in an adjacent layer. The fibers can be turned by 90 degrees, for example, so that a cross-shaped arrangement results. Multiple layers then form a cross-shaped fiber bundle.

The oxygenator modules are mostly produced by fixing the hollow fibers in casting compound. In the process, the casting compound is introduced into a mold, in which the fiber layers are arranged, and is arranged on an inner sheath surface by eccentric rotation of the mold due to centrifugal forces and cures therein and forms a so-called potting. In doing so, this process step is repeated for several sides of the fiber bundle, in particular four times, until the fiber bundle is enclosed and fixed from all sides by the potting. Thus, a cavity can be formed by the potting in which the fibers are arranged in a liquid-tight manner with respect to the surrounding and blood, for example, can flow around the fibers. Thereafter, the potting is removed from the mold. On the mold, so-called casting caps are provided on all sides which can be removed after the casting in order to expose the fibers. In doing so, the mold can be formed by the later (top and bottom) covers of an oxygenator on the one hand and the casting caps on the other hand. The outer sheath surfaces of the potting can be reworked in order to expose the ends of the fibers and make them accessible for gas loading.

Disadvantageous in these oxygenator modules is the fact that they can only be produced in a relatively expensive manner and that in the process, edges, transition regions and gaps between the individual sections of the potting can often also not be avoided in the cavity formed by the potting. This results in dead spaces in which perfusion cannot occur in a uniform manner which increases the risk of coagulation and reduces the period of application of the oxygenator module. It is also disadvantageous that the required quantity of casting compound at the individual sides of the module is to be selected in different sizes in certain cases so that the respective work step with the individual sides cannot be adjusted exactly the same. Rather, manual precise adjustments are required, whereby additional sources of error and variations in quality cannot be ruled out.

The task of the present invention is to provide a better apparatus for gas exchange between a gas and the blood of a human, animal or separate organ, in particular for extracorporeal lung support systems, as well as a better method for producing such an apparatus.

BRIEF SUMMARY

The aforementioned task is solved by an oxygenator module according to claim 1, an oxygenator according to the independent coordinate apparatus claim, and by a method according to the independent coordinate method claim respectively.

An oxygenator module for gas exchange between blood and a gas in an extracorporeal lung support system, with several layers of semipermeable, gas-perfusable hollow fibers, in particular membrane fibers, wherein the hollow fibers of one of the layers are oriented at an angle of rotation about a central longitudinal axis of the oxygenator module with respect to the hollow fibers of another one of the layers, and with a potting which extends along the central longitudinal axis and in which the hollow fibers are fixed, wherein the potting defines a cavity that extends along the central longitudinal axis and in which the hollow fibers are arranged and which is blood-perfusable in the direction of the central longitudinal axis, can be arranged in the extracorporeal lung support system in such a way that the blood can be introduced into the cavity on one side, circulates around the hollow fibers in the cavity, and can be drained from the cavity on another side.

According to the invention, it is provided that the potting has an inner sheath surface which has an essentially circular cross section and which limits the cavity radially outward.

Here, the inner sheath surface of the potting is designed in the shape of a circle with respect to a plane orthogonal to the central longitudinal axis. By means of the inner sheath surface with circular cross section, corners and dead spaces can be avoided. The circular inner sheath surface is preferably closed. It is designed as a surface that can be formed completely in a single solidification process. The circular, preferably cylindrical, inner sheath surface can preferably be produced by circular potting on a centrifuge. Here, "circular potting" is to be understood as a method in which the potting is given a circular, in particular cylindrical (inner) geometry. Thus, a circular potting is a potting which has on the inside toward the cavity a geometry that is as uniformly rounded as possible, wherein a radius of curvature of the potting across the circumference can also vary—at least within certain limits. By circular potting, a cylindrical module or a module with an essentially cylindrical cavity can be provided, which is designed essentially disk-shaped with a short extent toward the central longitudinal axis, i.e., rather flat and wide. The outer geometry of the potting can optionally be designed as round or even angular and is preferably also cylindrical.

Here, by means of hollow fibers that are arranged at an angle to one another, the gas exchange can be improved, especially since the blood must flow along flow paths which pass around the individual hollow fibers. The hollow fibers can cross each other in such a way that, in a plan view of the layers (viewed in the direction of the central longitudinal axis and orthogonal to the orientation of the hollow fibers), fewer or no direct or straight-line hollow spaces or passages from a blood inlet to a blood outlet exist. Here, the flowing blood comes into contact with a larger surface of hollow fibers. The arrangement of fibers in a cross-wise manner or at least rotated about the central longitudinal axis in connection with the circular inner sheath surface, in particular of a cylindrical cavity, promotes complete circulation around the fibers and thus efficient gas exchange. The hollow fiber layers can, for example, be designed as so-called membrane mats, in particular with a rectangular, for example quadratic, basic shape. Preferably, the basic shape of the hollow fiber layers is rectangular with different lateral lengths. In this way, the individual layers in adjacent layers rotated with respect to one another can respectively be exposed at the protruding ends in a certain angular range about the central longitudinal axis without the adjacent layer being exposed in the same angular range. This allows for the use of closed fibers which are opened at their free ends by rotationally cutting an outer sheath surface by rotation of a cutting device about the central longitudinal axis without the risk that they are cut open on their longitudinal sides. Furthermore, the side of the rectangular basic shape, parallel to which the hollow fibers are arranged, is preferably longer. Hereby, access to the fibers that are fixed within the potting and that are at least in part enclosed by the potting compound can be created in a simple manner.

Here, an axis around which the potting is arranged and alongside which the blood flows from an inlet through the cavity to an outlet is preferably to be understood as the central longitudinal axis.

The semipermeable hollow fibers can be loaded with an oxygen-containing gas and are oxygen-permeable. Here, a fiber that is gas-permeable (for example, permeable for gas diffusion), but liquid-tight, in particular blood-tight, is to be understood as semipermeable.

As potting material, polyurethane or silicone can be used, for example.

Here, a hollow fiber that is designed as semipermeable, thin capillaries with porous walls is preferably to be understood as a membrane fiber. It preferably has a cylindrically designed shape with an inner cylindrical hollow space. In case of microporous membranes (in particular for short-time applications), stretched polypropylene (PP) can be used, for example. In case of plasma-tight membranes for long-time application, polymethylpentene (PMP) with a plasma-tight film on the (blood-side) surface of the fibers can be used, for example. Preferably, PMP-based fibers are used.

Here, an apparatus which makes possible the exchange of gas components between the blood and a gas, in particular oxygen and carbon dioxide, that is routed in the blood in a conduit system, in particular hollow fiber membranes, is to be understood as an oxygenator module. An oxygenator module has fiber layers or fiber mats which are arranged in the oxygenator module, for example, in layers one on top of the other, folded and/or laid and form a laid oxygenator module. Here, an oxygenator module in which the individual layers of hollow fibers are arranged one on top of the other and form bundles is to be understood as a laid oxygenator bundle. The oxygenator module furthermore has a potting in which the fibers are embedded. Optionally, the oxygenator module can also have one or several covers for sealing the cavity formed by the potting.

Preferably, the inner sheath surface of the cavity or the potting along the central longitudinal axis is arranged at a constant radial distance to the central longitudinal axis, i.e., the inner sheath surface is designed cylindrical so that a cylindrical geometry is given to the cavity by the potting. By means of the cylindrical inner sheath surface of the circular potting, it can be avoided that dead spaces that can be perfused by blood a little or not at all form at corners or in recesses. By means of a cylindrical cavity, uniform perfusion can be ensured. Sections that are not perfused or perfused only a little (so-called dead water areas) can be avoided, whereby the risk of coagulation is reduced and the period of application of the oxygenator module is extended.

The layers are preferably arranged in planes that extend at an angle of 45 to 90 degrees, in particular at least approximately orthogonally, to the central longitudinal axis. In this way, they can on the one hand be fixed in the potting compound well; on the other hand a large number of fibers can be arranged in a cavity with a predetermined internal volume. Preferably, the layers are arranged in planes that are parallel to one another. The hollow fibers of a plane can furthermore be arranged at least approximately orthogonally to the hollow fibers of an adjacent layer so that a cross-shaped fiber bundle is formed. This (in particular cross-shaped) arrangement provides good fluidic properties and can additionally be produced easily. According to a preferred variant, the fibers of one layer are arranged at an angle of at least approximately 45 or 60 degrees to the fibers of an adjacent layer, where preferably three or four consecutive layers are each rotated by an angle of 45 or 60 degrees about the central longitudinal axis.

Furthermore, the layers are preferably staggered with respect to one another in the radial direction so that, viewed in a flow direction, the blood strikes the hollow fibers directly, around which it must circulate. Such an arrangement can be referred to as a static mixer. In this way, it can be avoided that the blood stream mainly occurs alongside channel-like hollow spaces in the cavity and does not completely circulate around the fiber surface. The radially staggered arrangement can be provided in connection with the cross-shaped arrangement or the arrangement rotated by an angle of 45 or 60 degrees.

Here, the gas is in particular oxygen or an oxygen-containing gas or even ambient air. The hollow fibers can be of the type of membrane fibers for an oxygenator, but other fibers can also be used, in particular if the module is not intended for an oxygenator, but for other, yet similar applications, for example for a heat exchanger, a hemofilter, a dialysis machine, an arterial filter or for combined devices, i.e., devices with, for example, both a gas-exchange and a heat-exchange function.

According to the invention, the layers are each arranged so that they overlap one another, where at least one free end of the layers respectively protrudes from a directly adjacent layer in a non-overlapping region. For this purpose, the layers preferably have a rectangular basic shape with different lateral lengths. Preferably both free ends of the layers respectively protrude from an adjacent layer in a non-overlapping region. Furthermore, the partly overlapping layers are preferably provided in the fiber bundles or fiber layers that are arranged in a cross shape or rotated by an angle of 45 or 60 degrees with respect to one another. By means of an only partially overlapping arrangement, the free ends of the fibers can be arranged especially close to an inner wall of a preferably essentially cylindrical mold into which the potting compound is introduced. In this way, potting compound can be saved on the one hand; on the other hand, a process step for exposing the fiber ends can be easily saved or at least be performed easily or quickly. According to a variant, the layers can also have a circular geometry, in particular with respect to the region that is surrounded by the potting compound. In other words, each layer can form a complete cross sectional area of the cavity.

The advantage of partially overlapping layers can be described using the example of the layers arranged rotated by 45 or 60 degrees to one another, where each layer has a rectangular basic shape with different lateral lengths. The respective layers are preferably superposable. Three or four layers respectively together have three or four different regions or sections of different fiber density. In a core region, all three or four layers overlap one another. Here, the core region, which has the highest fiber density with respect to the taken-up volume of the cavity, preferably has a hexagonal basic shape. In a respective, protruding region or section, none of the three or four layers overlaps the other layers. In total, six or eight of these non-overlapping, exposed sections are formed. The non-overlapping, exposed sections each have, in a 60-degree arrangement, for example, a triangular geometry with a rectangular section that is radially outward directly adjacent to it. In these section, the fiber density is lowest. Furthermore, partially overlapping sections are also formed, in which two of the three layers or three of the four layers overlap one another. The partially overlapping sections each have, in a 60-degree arrangement, for example, a triangular geometry.

According to a preferred embodiment, the potting has a particularly cylindrical outer sheath surface from which the hollow fibers protrude radially with at least one free end. In this way, the oxygenator module can be produced on the one hand with few work steps; on the other hand, the fiber ends can all have the same geometry. A separating, particularly a cutting of (the free ends of) the hollow fibers is not necessarily required. The fiber ends are, for example, not provided with a bur by a cut or embrittled or broken or elliptical. Here, the fiber ends can, for example, also be designed with a certain geometry, for example slightly conical or with a chamfer in order to design the inflow of gas to be particularly uniform. In case the fiber ends are not yet open, cutting of the fiber ends can take place easily, especially since the fiber ends are exposed and are not cast in the casting compound.

Preferably, the outer sheath surface is designed to be cylindrical. Here, a sheath surface that has an at least approximately circular geometry in the cross section is to be understood as a cylindrical outer sheath surface. Furthermore, the potting is preferably designed in a tubular shape. Here, a tubular potting is formed by a completely cylindrical inner sheath surface and a completely cylindrical outer sheath surface. With a cylindrical outer sheath surface, the fiber ends can easily be kept or made accessible, in particular by machining the outer sheath surface with a cutting device that rotates relative to the oxygenator module.

At least two of the layers can be formed from a folded fiber mat, where the hollow fibers of the folded fiber mat can be arranged in several of the layers. In other words, one (long) hollow fiber each is arranged in at least two different layers. A folded fiber mat can, for example, be formed by a garland fold of two small mats made from long hollow fibers. Alternatively, a folded fiber mat can, for example, also be formed by a folding of two mats with empty, regularly repeating fiber positions, i.e., hollow fibers bundled into individual packages. One advantage with folded layers is the fact that the step of separating into individual layers can be dispensed with, since this step is unnecessary depending on the design of the fiber ends or can take place in connection with an opening or cutting of the fiber ends. The long hollow fiber can optionally be divided again by cutting after a potting so that in each layer, the hollow fibers are permeable independently of one another.

According to an embodiment, which can be combined with one of the previously described embodiments, the hollow fibers of each layer have two free ends and protrude with both free ends from the potting, particularly the outer sheath surface. Here, the fibers are preferably open at their two free ends or were opened particularly by cutting. In this way, the oxygenator module can be manufactured in a cost-efficient manner and/or with few process steps. An opening of the hollow fibers, particularly by cutting, is no longer required. Here, hollow fibers which in the unprocessed state as half-finished products are already provided in non-closed form, i.e., they do not have to be opened by cutting the free ends, are to be understood as open hollow fibers. If one hollow fiber layer is produced by laying an endless fiber in a meandering pattern and fixing it with warp threads, then closed ends are usually present that have to be cut open.

According to one embodiment, which can be combined with one of the previously described embodiments, at least two of the layers are formed from a folded hollow fiber mat, where the hollow fibers in the hollow fiber mat are arranged as hollow fiber packages with a distance to one another and connected with one another by means of warp threads. In other words, the (short) hollow fibers of the fiber mat are respectively bundled together into packages which form one of the layers, and each layer is independent of the other layers. In this way, a fiber bundle with only partially overlapping layers can be provided easily.

According to one preferred embodiment, which can be combined with one of the previously described embodiments, the oxygenator module has an outer geometry with more than four corners, in particular a hexagonal or octagonal outer geometry. By means of this geometry, the exchange surface provided by the fibers can be used especially well, particularly in connection with a cylindrical cavity. The outer geometry can, in a practical manner, be provided in connection with an advantageous arrangement of the layers at an angle to one another. Preferably, the outer geometry is formed by both the potting and the at least one cover.

According to one preferred embodiment, which can be combined with one of the previously described embodiments, at least two, preferably at least three, of the layers are arranged rotated at an angle unequal to zero and smaller than 90 degrees to one another, particularly rotated about the central longitudinal axis, preferably at an angle of at least approximately 45 or 60 degrees. This arrangement can ensure an especially effective use of the fiber surface as exchange surface. When stacking the layers at an angle of 90 degrees in a cylindrical cavity, a majority of the fibers would already be surrounded by potting compound. In this way, a smaller percentage of the fibers is in contact with blood. In comparison to such a cross-shaped (orthogonal) arrangement, in a 45-degree or 60-degree arrangement, the surface of the fibers or the available space or the volume of the cavity can be used especially effectively, particularly in connection with a cylindrical cavity. In comparison to a cross-shaped (90-degree) arrangement, there are even less dead spaces or free spaces where only a reduced exchange can occur. The angle of rotation is preferably significantly lower than 90 degrees and preferably amounts to a maximum of 60 degrees. The angle of rotation must however not necessarily be exactly 45 degrees or 60 degrees, but can also be greater than 60 degrees or smaller than 45 degrees.

The arrangement rotated about 45 or 60 degrees can ensure that the fibers are arranged in three or four different orientations, where in each of the three or four differently oriented fiber layers a specific fluid can optionally be routed. For example, one of the three or four fiber layers can be perfused with water, particularly when functioning as a heat exchanger. In doing so, three or four different flow directions can be provided. According to one variant, the fibers or the fiber material of the respective layer is a specific fiber material which is optimized, for example, with respect to the fluid/medium to be routed.

In the arrangement rotated about 45 or 60 degrees, edge regions can be provided with a lower fiber density compared to the core region, where a preferred flow can be adjusted in the edge regions, which has advantages for the exchange, especially with a large cross-section geometry. In other words: usually the flow rate is lowest where the distance to the flow inlet/outlet is largest. A low flow rate frequently also means a larger risk of coagulation so that variations in the flow rate should be avoided if possible. With central inflow, the flow rate is particularly lower in the edge region of the cavity than in the center. The larger the diameter of the cavity, the larger the variation of the flow rate between the center and the edge of the cavity. Due to the lower fiber density in the edge region, the flow resistance in the edge region can be reduced, for example to $1/3$ or $2/3$ of the flow resistance at maximum fiber density, whereby a comparably larger flow rate can be adjusted in the edge region. The stream preferably flows through this edge region with lower resistance (preferred flow). Here, depending on the value of the angle of rotation of the fiber layers, the flow differences between the center and the edge region can be compensated so that a homogeneous flow field can be realized and the residence times or contact times can be adjusted.

In addition, in the arrangement rotated about 45 or 60 degrees, fiber material can also be saved. A housing can also be designed in an especially compact manner.

Preferably, all hollow fiber layers are arranged rotated to one another, particularly adjacent hollow fiber layers that are directly above one another, at an angle of rotation of at least approximately 45 degrees or 60 degrees respectively.

Preferably, the oxygenator module has a hexagonal outer geometry or peripheral geometry, where each side or edge of the peripheral geometry is preferably defined by the exposed fiber ends of each fiber layer.

According to one variant, different angles of rotation can be combined with one another, particularly in one single oxygenator module as well.

A multi-fluid fiber apparatus, in particular an oxygenator, can be designed with at least one oxygenator module according to the invention. Here, several oxygenator modules can optionally be arranged in a row one behind the other.

An oxygenator module, preferably an oxygenator module with the properties described above, can be provided in an oxygenator for the gas exchange between blood and a gas in an extracorporeal lung support system, with a blood inlet and a blood outlet, respectively coupled (in communication) with a blood-perfusable cavity of the oxygenator module, and with a housing to accommodate the oxygenator module, wherein the housing has a gas inlet and a gas outlet, each of which is coupled to the hollow fibers of the oxygenator module, i.e., the gas inlet and the gas outlet are in fluidic connection with the hollow fibers.

It is suggested that the oxygenator has a distributor device which is arranged, with respect to the central longitudinal axis of the oxygenator module, upstream of the at least one oxygenator module and downstream of the blood inlet, wherein the oxygenator is set up for a central inflow of the oxygenator module. In this way, the blood stream can be distributed more homogeneously over the hollow fiber bundle, and homogeneous perfusion can be ensured in an effective manner. Here, in a circularly potted oxygenator with cylindrical cavity, the radial distance of the blood inlet to the edge region is the same in all radial directions.

According to one embodiment, the blood inlet and/or the blood outlet are arranged centrally with respect to the oxygenator module, particularly with respect to the cavity. In this way, a homogeneous perfusion and a homogeneous expansion of the stream is ensured. According to one variant, the distributor device has the blood inlet and is arranged on the oxygenator module in such a way that the oxygenator module can be fed centrally.

According to an embodiment, the distributor device has a swirl distributor and is designed to guide a blood stream with a swirl at a flow angle to the central longitudinal axis into the cavity. In this way, the blood stream is guided into the cavity such that the risk of dead spaces is reduced. Furthermore, the gas exchange can, for example, be improved in the range of 5 to 12 percent with respect to the previously known oxygenators. By means of a homogeneous perfusion or a uniform distribution of the flow rates across the perfused area, the residence time can be adjusted more uniformly.

The swirl distributor is designed to guide the blood stream into the cavity on a flow path which is oriented at a flow angle to the central longitudinal axis. Here, the flow path does not necessarily run from the blood inlet directly to the blood outlet, but can be longer than the direct path. In this way, the gas exchange is improved. The swirl distributor is arranged in a row with the oxygenator module. Preferably the swirl distributor is fed centrally and is designed symmetrically in the radial direction, particularly with an equal radial distance to an inner sheath surface of the potting or cavity on all sides.

Preferably, the flow angle is in the range of 30 to 90 degrees, more preferably 45 to 85 degrees, especially preferably 65 to 80 degrees. In this way, improved, more complete circulation of the fibers can be achieved, in particular with a cylindrical inner sheath surface of a cavity. It can also be ensured that all regions of the cavity are perfused. Here, it can be avoided, for example, that blood flows essentially only form in the center of the cavity. Preferably, the strength of deflection is selected as a function of the radial extent of the cavity, where the deflection is stronger when the radial extent is greater.

Here, preferably a device, arranged statically with respect to the oxygenator housing, for the deflection of the blood stream, where the deflection can take place, depending on the arrangement of the fibers, at up to 90 degrees, is to be understood as a swirl distributor. In this way, the blood can be put into a rotation on the one hand, on the other hand can be guided through the oxygenator laterally as well, i.e., at an angle with respect to the central longitudinal axis, and can flow along the hollow fibers across a longer path. The swirl distributor allows for an areal spreading of the blood stream. In particular with fibers or layers that are arranged in a cross shape or rotated by 45 or 60 degrees with respect to one another and with a cylindrical inner sheath surface, it is advantageous to deflect the blood stream and to guide it at least approximately in the circumferential direction along the inner sheath surface as a larger proportion of the length of the hollow fibers in the direction of extent of the fibers can thereby be circulated.

A swirl distributor has preferably a cylindrical outer sheath surface. In this way, it can easily be coupled or connected with an oxygenator module with a cylindrical inner sheath surface and an optionally cylindrical outer sheath surface as well.

The gas inlet and gas outlet are preferably arranged such that a gas stream can be directed toward the front of the free ends of the hollow fibers. Here, gas can be introduced by negative pressure and/or positive pressure, i.e., in a sucking or blowing manner. The potting can hereby be mounted in the housing on an inner sheath surface of the housing and/or can be mounted in the housing by means of one or several covers and/or can be glued to the housing. The inner sheath surface of the housing can be designed at least partially cylindrically, in particular with a cylindrical part that is protruding radially inward and on which the potting can be mounted, without the fiber ends coming into contact with the inner sheath surface.

According to one embodiment, which can be combined with one of the previously described embodiments, the swirl distributor has an inner sheath surface with circular cross section as well as internal swirl elements that merge into one another toward a central point of the swirl distributor. In this way, deflection of the blood stream can take place in an especially effective manner and at large deflection angles so that the blood stream can be guided laterally into the cavity with as large as possible a flow angle in the range of 90 degrees.

According to one embodiment, which can be combined with one of the previously described embodiments, the swirl distributor has swirl elements in the form of wings, particularly four to six wings. In this way, the blood stream can be deflected evenly across the entire cross section of the swirl distributor. Here, the number of wings can be selected as a function of the geometry or dimension of the cavity, where the wings centrally border on each other and form a deflector surface.

According to one embodiment, which can be combined with one of the previously described embodiments, the oxygenator has, upstream of the distributor device, a cover which has a pyramidal or conically tapering geometry in the direction of the central longitudinal axis. In this way, the blood stream can be evenly expanded or widened from a blood inlet up to the oxygenator module and can be spread across the entire cross section.

According to one preferred embodiment, the oxygenator has at least one cover, which is fixed by means of a/the potting of the oxygenator module. In this way, it can be ensured that the oxygenator module, particularly an outer sheath surface of the potting or fiber ends, can be reworked in an especially practical manner. In particular, the advantage results that the fibers are not exposed during processing and cannot be damaged or soiled. Here, the cover has preferably a hexagonal outer geometry. By means of this geometry, the (respective) cover can be arranged together with the layers in a casting mold in a practical manner, where the cover(s) can be fixed together with the layers by means of the potting compound, in particular in connection with a cylindrical cavity and a 45-degree or 60-degree arrangement of the layers. The cover preferably has an outer geometry, which is designed to be geometrically corresponding to the outer geometry of the potting.

According to one embodiment, which can be combined with one of the previously described embodiments, the distributor device has an aspect distributor or a tangential distributor or a distributor for an expansion of the blood stream respectively. The expansion takes place in the radial direction orthogonally to the central longitudinal axis. In this way, the blood stream can be spread areally onto the swirl distributor so that the swirl distributor can more effectively deflect the blood stream. The aspect distributor or tangential distributor can be used alternatively to the swirl distributor. However, the aspect distributor is preferably used in connection with the swirl distributor and arranged in particular upstream of the swirl distributor. The aspect distributor itself can have one or several swirl elements and be developed into a swirl distributor in this way. The tangential distributor has no swirl elements and provides the advantage that with a lateral inflow and rotation of the blood stream, air bubbles are avoided that cannot escape, but that can escape in the axial direction in the center of the tangential distributor. Another advantage is the comparably low construction height of the tangential distributor.

The aspect distributor has a central opening or orifice which is small in relation to its radial dimensions. The radial dimension of the orifice is preferably at a ratio of 1:5, more preferably 1:10, in respect of the absolute radial dimension of the aspect distributor. The tangential distributor has a central opening or orifice which is small in relation to its radial dimensions. The radial dimension of the orifice is preferably at a ratio of no more than 1:7, more preferably 1:12 or 1:15, in respect of the absolute radial dimension of an inner sheath surface of the tangential distributor.

According to one embodiment, which can be combined with one of the previously described embodiments, the distributor device has a distribution element with a plurality of openings, in particular a circular blood distributor plate which is designed to be geometrically corresponding to the cavity. Such a distribution element can be arranged in a space-saving manner between other components of the oxygenator and can distribute the blood stream efficiently across the entire cross section by means of a simple measure.

The aforementioned task is also solved, as mentioned, by a method according to the dependent coordinate method claim.

By a method for producing a module for a multi-fluid fiber apparatus, particularly an oxygenator module for an oxygenator of an extracorporeal lung support system, with the following steps:

a) arranging a majority of hollow-fiber layers within a (casting) mold, where the hollow fibers of one of the layers are oriented at an angle of rotation about a central longitudinal axis of the oxygenator module to the hollow fibers of another one of the layers;

b) arranging the mold with respect to an axis of rotation of a centrifuge;

c) feeding potting compound into the mold;

d) rotating the mold about the axis of rotation in order to exert a centrifugal force on the potting compound in order to arrange the potting compound radially outward in the mold, particularly at the same time as step c);

e) curing the potting compound in order to fix the hollow-fiber layers, particularly in continuous rotation;

f) removing the potting compound together with the hollow fiber layers from the mold or at least from a part of the mold;

an oxygenator module for an extracorporeal lung support system can be provided.

According to the invention, it is provided that in step b), the mold is arranged about the axis of rotation in such a way that the axis of rotation lies within the mold, whereas in step d), a cavity with an essentially circular inner sheath surface of the potting compound is formed. In this way, a uniform circular potting without gaps, angular transitions or other discontinuities that promote dead spaces can be provided. In particular, a perfusable region with circular, cylindrical cross-section geometry can be provided, which can be perfused evenly by blood.

According to one embodiment, the layers in step d) can be embedded in the potting compound in such a way that they are arranged partially overlapping each other. By means of the (only) partially overlapping arrangement of the layers relative to one another, it can be ensured that each of the layers can be embedded in vicinity of the fiber ends. The fiber ends protrude from the overlapping core region. Even in a straight-line arrangement of the fiber ends, each layer can be embedded with comparably little potting compound when viewed in the radial direction. Furthermore, a respective layer can also be embedded in the potting compound securely, because more potting compound can surround the layer at the top or at the bottom than with a fiber density that corresponds to the fiber density in the core region.

Here, the potting material is introduced into a casting mold. The casting mold can be characterized in particular by the following features, whether individually or in combination with one another:
- symmetrical structure, in particular to avoid imbalances;
- two-part, in particular for introducing or removing components, such as covers or fiber layers;
- liquid-tight;
- inner geometry with more than four corners, preferably a hexagonal inner geometry;
- draft angles;
- openings for ejecting the module;

Here, the casting mold can have a co-rotating distributor chute with preferably four to six outlets.

Here, the axis of rotation is arranged at a radial distance to the inner sheath surface of the mold. The distance of the axis of rotation to the mold is preferably larger than the minimum thickness of the potting in the radial direction to be attained. In step b), the mold is preferably arranged centrally about the axis of rotation. In this way, a potting with uniform wall thickness can be provided. Contrary to an eccentric potting, at least one work step can also be saved here because the potting can completely take place without the mold having to be positioned anew (repositioned) on the centrifuge. The potting can take place completely in one process step with respect to all sides of the hollow fiber layers or the fiber bundles. In this way, the fiber bundle can also be fixed more precisely within the potting, as an interruption of the process can be avoided at a time when the fiber bundle would only be fixed in the potting compound on one side. Furthermore, the inner diameter of the cavity can be adjusted easily as it is only necessary for this purpose to select a certain amount of potting compound. Here, there is also the advantageous effect that the individual hollow fibers are not compressed or bent, but are at most stretched due to the centrifugal force, whereby the position of the hollow fibers with respect to one another can be adjusted more exactly or precisely. This also ensures a homogeneous circulation of the hollow fibers.

The inner sheath surface is designed to be, with respect to a plane orthogonal to the central longitudinal axis, at least approximately circular so that a uniformly perfusable cavity can be provided. The cavity has no undercuts, edges or other discontinuous transitions. Here, the hollow fiber layers can be arranged partially overlapping one another and free ends of the layers respectively protrude from an adjacent layer in a non-overlapping region.

Here, an arrangement central with respect to one axis of rotation of the centrifuge is to be understood as a central arrangement. The arrangement can, for example, take place on a rotary disk or in another centrifugal device.

Furthermore, the potting can take place in a single work step or in significantly lesser work steps compared to previously known methods. This saves time and/or costs and the manufacturing process can be automated easily. Potting of each individual of the four lateral surfaces as with an (in particular laid) oxygenator module with a rectangular cross section, for example, or potting of both sides as with a wound oxygenator module does not take place. Rather, potting of a cylindrical inner fiber bundle can take place by provision of a cylindrical annular potting area radially outward on the fiber bundle. Here, a cylindrical cavity can also be provided with an angular external shape by means of the potting.

Here, a casting of fiber mats or an alternative material provided for the gas transport within the blood is preferably to be understood as a potting.

Here, any static arrangement of hollow fibers in potting compound that can be used in an apparatus with a medical function is preferably to be understood as a module for a multi-fluid fiber apparatus. For this purpose, apparatuses of the type membrane contactor or membrane filter, for example, can also be included in addition to an oxygenator module.

The introduction of potting compound takes place preferably while rotating the module or oxygenator module. By introducing the potting compound only when the mold is already being rotated and a centrifugal force is present, it can be easily avoided that the potting compound comes into contact with fiber regions that are not to be potted.

Here, a medical apparatus in which hollow fibers arranged in a blood-perfusable cavity can be circulated in order to allow for an exchange of gas or energy between the blood and a gas conducted in the hollow fibers, in particular an oxygenator, a heat exchanger, a hemofilter, a dialysis machine, an arterial filter or even a combined apparatus with, for example, both an oxygenator and a heat exchanger, is preferably understood as a multi-fluid fiber apparatus. Two gases or two liquids that can also be of the same type can also be used as fluids.

In step f), the potting compound does not necessarily have to be removed from all mold parts. Rather, a cover can also form a part of the casting mold, the cover then being firmly connected to the hollow fiber layers after the potting and being removed together with the potting compound from other mold parts.

According to one embodiment, the mold is used as a female mold for forming an outer sheath surface of the potting compound. In this way, the potting can be given a certain outer geometry. A cylindrical outer sheath surface is preferably formed by using a cylindrical female mold that is arranged concentrically about the axis of rotation. Here, the outer sheath surface can be formed by the female mold itself or optionally indirectly by arranging a barrier fluid between the female mold and the potting compound.

According to a preferred embodiment, in step a), at least one cover is also arranged in the mold in such a way that in steps d) and e), the potting compound fixes the at least one cover to delimit the cavity. The potting of the layers together with one or several covers provides an efficient method and can also ensure a simple structure of the oxygenator. Here, an additional (support) frame is not required. Here, the potting compound can, together with the at least one cover, form a hermetically sealable cavity. This is advantageous in further work steps, in particular in chip-forming work steps.

The circularly potted oxygenator module can optionally be processed in another work step by cutting, particularly to give the outer sheath surface of the oxygenator a polygonal or round geometry. Here, closed fibers can also be used which can be opened by cutting the potting so that they are accessible and can be loaded with a gas. Here, the hollow fibers can be delivered by a manufacturer on spools. Here, a single hollow fiber layer can be formed by individual hollow fibers that are worked into mats in a meandering pattern, where the hollow fibers at the ends of the mats or in the edge region of the respective layer are sealed or bent. The separation into several fibers can take place by cutting after the potting. In connection with a cylindrical outer sheath surface of the potting, a method for cutting or exposing the hollow fibers can be simplified, particularly because the outer geometry prior to the cutting is already provided at least approximately in the later target geometry. Here, the cutting allows for comparably straight cut surfaces.

The circularly potted oxygenator is preferably given a round geometry, particularly by rotating it (like a turned part during a turning process on a turning machine) about its own central longitudinal axis. Here, the central longitudinal axis can correspond to the axis of rotation of the centrifuge. Here, during rotation of the oxygenator, a cutting device, such as for example a blade, can be brought toward the oxygenator or the oxygenator itself can be brought toward a fixed cutting device in order to shave off part of the potting from the outside of the oxygenator. The cutting device itself can also be rotated about the oxygenator. The movements mentioned can also be combined with one another. Here, the cutting can also comprise a peeling of the hollow fibers, i.e., not only a shaping of the potting, but also an opening of the hollow fibers. In doing so, an advance and the rotational speed can be adjusted, especially by means of a control device, so that the peeling can take place with a definable peeling depth.

According to one embodiment, which can be combined with one of the previously described embodiments, a barrier fluid that has a higher density than the potting compound is arranged on an inner sheath surface of the mold prior to step c). In this way, a process step for exposing the fibers can be simplified or saved. Here, closed or open hollow fibers which protrude from the potting compound in the region of the free ends of the hollow fibers can optionally be used. Closed hollow fibers can be more easily exposed as potting compound does not have to be peeled off in this process, and with open hollow fibers, a cutting or exposing can be eliminated completely.

Due to the higher density of the barrier fluid, the barrier fluid can, during rotation of the mold, be pushed outward by the centrifugal force more strongly than the potting compound so that the barrier fluid and the potting compound are not mixed but, metaphorically speaking, are arranged just like a water-oil mixture where the oil is always at the surface of the water. By means of the difference in density, it can be avoided, for example, that an emulsion forms. As barrier fluids, crystalloid solutions with a higher specific gravity than polyurethane or the potting compound used can be employed, for example.

The barrier fluid can in particular be fed in during rotation of the mold so that it is arranged on the inner sheath surface of the mold due to the centrifugal forces. Here, the amount of barrier fluid is preferably adjusted in such a way that the free ends of the hollow fibers are arranged in the barrier fluid. This ensures that the free ends are not closed by the potting compound. The barrier fluid is fed in during rotation of the module, for example, before the potting compound is fed in. Here, a feeding of the potting compound takes place preferably in the axial direction, i.e., not radially from the side. Optionally, the barrier fluid can also be fed in after introduction of the potting compound and can displace the potting compound at the inner sheath surface of the mold. According to one variant, the barrier fluid can also already be provided in the mold before the hollow fiber layers are arranged in the mold. In this process, in the repeated manufacturing of a module with the mold, a barrier fluid can also remain in the mold and be used several times.

According to one embodiment, which can be combined with one of the previously described embodiments, the barrier fluid is drained between step e) and step f). In this way, the module can dry in the mold more quickly or can be dried actively by means of a convective air flow, for example, before it is removed. According to one variant, the barrier fluid can be drained during step e), in particular in order to allow for faster drying or curing. In this process, a drying of the fibers itself is not required. The curing is carried out for the case of polyurethane as potting compound preferably in a chemical manner by generating heat (exothermic reaction), particularly in continuous rotation. Draining preferably does not occur during step e) until the potting compound is already set at least to a certain extent. Draining during step e) can also result in faster curing of the potting compound, in particular because air circulation can also take place or heat can be introduced at an outer sheath surface of the potting, for example. The barrier fluid is preferably removed from the mold during step e) as soon as the potting compound is partially cured such that it is inherently stable. Closed hollow fibers are preferably used to easily ensure that no barrier fluid can enter the hollow fibers. The barrier fluid is preferably biocompatible. In this way, it is not necessary, for example, to rinse with another liquid.

According to one embodiment, which can be combined with one of the previously described embodiments, at least two, preferably at least three, of the hollow fiber layers are arranged rotated at an angle unequal to zero and smaller than 90 degrees to one another, particularly rotated about the central longitudinal axis, preferably at an angle of at least approximately 45 or 60 degrees. In this way, the fiber material can be made particularly good use of, especially with a cylindrical cavity.

According to one variant, the mold is rotated until the potting compound has solidified to such an extent that it is at least inherently stable. The oxygenator module is then removed from the mold without draining the barrier fluid beforehand. In this way, a large number of modules per time unit can be manufactured with the same mold, which reduces the piece costs. At the same time, a drying or setting of the potting compound can be performed independently of the process step of shaping within the mold. In this way, process parameters, such as temperature or air circulation for drying, can be adjusted more flexibly during drying and curing.

According to one variant, the oxygenator module is first connected to one or two covers before it is removed from the mold. The covers can form part of the casting mold.

The present invention also relates to the use of an oxygenator module according to the invention or an oxygenator with an oxygenator module according to the invention in an extracorporeal lung support system. The oxygenator can be used to treat humans or animals or even any isolated (donor) organ. Vital functions of the (donor) organ can be maintained completely isolated from the donor or the recipient (human/animal), for example, using the extracorporeal lung support system.

The present invention also relates to the use of a cylindrical fluid-tight female mold for shaping the outer sheath surface of a potting of a module for a multi-fluid fiber apparatus, preferably an oxygenator module according to the invention.

BRIEF DESCRIPTION OF THE SEVERAL VIEWS OF THE DRAWINGS

In the following figures, the invention is explained in more detail using exemplary embodiments, where various components for an oxygenator according to the invention are shown, a different module on the one hand, various flow devices on the other hand (swirl distributor and aspect distributor). If individual reference symbols are not explicitly explained in connection with the figures, reference is hereby made to the respectively other figures. They show:

FIG. 4a a schematic plan view of a fiber bundle, that is arranged in a mold for producing an oxygenator module according to one exemplary embodiment of the invention, with hollow fiber layers with rectangular basic shape with different lateral lengths;

FIG. 4b a schematic plan view of the mold shown in FIG. 4a with potting compound introduced into it and arranged at an inner sheath surface of the mold;

FIG. 5a a schematic plan view of the oxygenator module produced by means of the mold shown in FIG. 4b;

FIG. 5b a schematic plan view of the oxygenator module shown in FIG. 5a in a process step, in which the potting of the oxygenator module is processed by means of a cutting device;

FIG. 5c a schematic plan view of the oxygenator module of FIG. 5b processed by cutting;

FIG. 6a a schematic plan view of a fiber bundle, that is arranged in a mold for producing an oxygenator module according to one exemplary embodiment of the invention, with hollow fiber layers with rectangular basic shape with different lateral lengths;

FIG. 6b a schematic plan view of the mold shown in FIG. 6a with potting compound introduced into it as well as barrier fluid introduced into it, which is arranged at an inner sheath surface of the mold outside the potting compound;

FIG. 6c a schematic plan view of the oxygenator module of FIG. 6b with a potting that was shaped by means of the barrier fluid and from which the hollow fiber layers protrude;

FIG. 7a a schematic perspective view of an oxygenator with an oxygenator module according to one exemplary embodiment of the invention;

FIG. 7b a schematic sectional view of the oxygenator shown in FIG. 7a;

FIG. 9b another schematic perspective view of the aspect distributor shown in FIG. 9a;

FIG. 10 a schematic perspective view of a tangential distributor for an oxygenator according to one exemplary embodiment of the invention;

DETAILED DESCRIPTION

Figure 1:
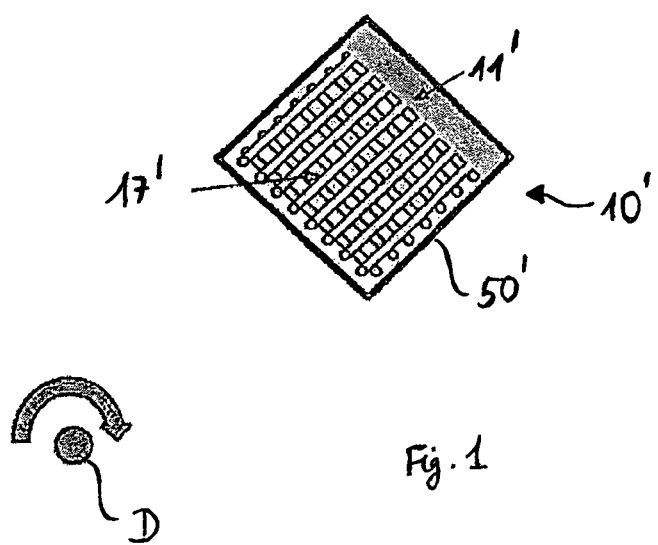
FIG. 1 a schematic plan view of an oxygenator module according to the prior art which is arranged in a mold on a centrifuge eccentrically to the axis of rotation of the centrifuge.

In FIG. 1, a fiber bundle 17' arranged in a mold 50' is shown, wherein the mold 50' is arranged on a centrifuge (not shown) and is rotated about an axis of rotation D of the centrifuge. Hereby, an oxygenator module 10' is to be produced step-by-step. FIG. 1 shows the prior art. A rectangular, particularly quadratic mold 17' is used. Firstly, one of the four lateral surfaces of the oxygenator module 10' is provided with a potting 11' by introducing potting compound for one of the four sides of the fiber bundle 17' into the mold 50' and by rotating the mold 50' about the axis of rotation D. A centrifugal force acting as a result of the rotation affects the potting compound and drives it to the point that is located furthest radially outward. This is at least in rough approximation the (entire) lateral surface of the mold 50' located radially outward. In the process, the outer surface of the potting 11' takes on the geometry of an inner surface of the lateral surface of the mold 50' located radially outward. Here, the mold 50' is arranged eccentrically to the axis of rotation D in order to achieve an essentially even inner sheath surface. As soon as the potting compound is inherently stable, i.e., at least somewhat solidified, the rotation can be interrupted and the form 50' can be arranged rotated by 90 degrees about its own central longitudinal axis in order to pot another one of the lateral surfaces. In doing so, the fiber bundle 17' is braced in the axial direction between two blood covers (not shown) to avoid that the fiber bundle 17' is turned relative to the longitudinal axis. The steps can be repeated until all four sides are potted and the fiber bundle is completely fixed in the potting 11'.

Figure 2A:
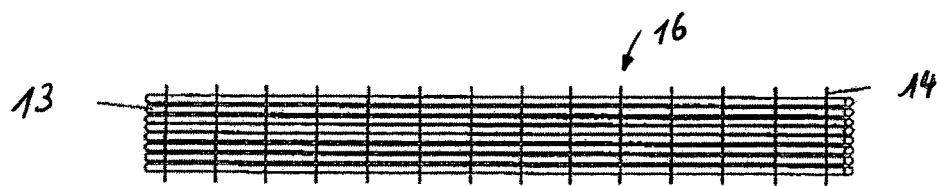
FIG. 2a a schematic plan view of a hollow fiber mat with long fibers which are suited to form a fiber bundle for an oxygenator module according to the invention.

In FIG. 2a, a hollow fiber mat 16 is shown, which is formed from a plurality, in particular eight, fibers 13 arranged next to one another, whereby the fibers 13 are connected with one another via warp threads 14. The warp threads 14 extend orthogonally to the fibers 13. The number of fibers can be up to 200, with only eight fibers being shown in FIG. 2a for reasons of clarity.

Figure 2B:
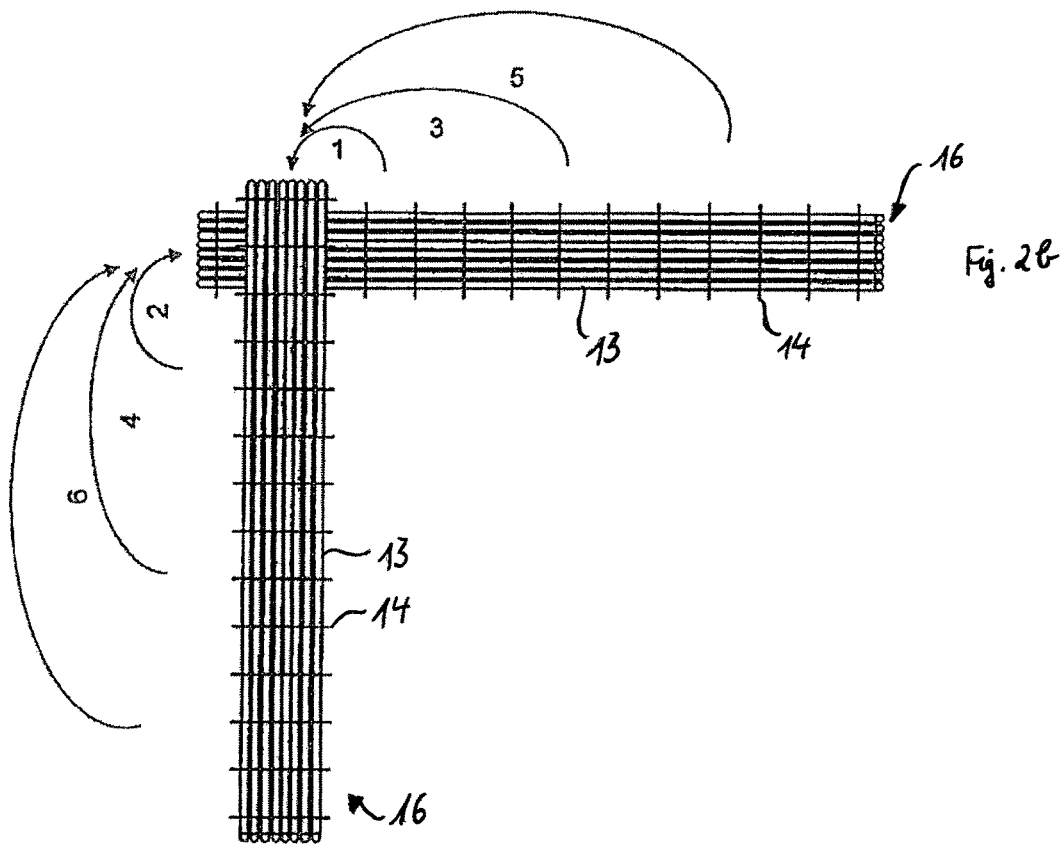
FIG. 2b a schematic plan view of a hollow fiber mat with long fibers which can be folded with another hollow fiber mat with long fibers to form a fiber bundle for an oxygenator module according to the invention.

In FIG. 2b, another hollow fiber mat 16 is shown that is arranged on another hollow fiber mat 16 rotated by 90 degrees with respect to the latter and has the same structure. The two hollow fiber mats 16 can be folded into one fiber bundle by initially folding over the lower hollow fiber mat (arrow 1) and then making additional foldings (arrows 2, 3, 4, 5, and 6).

Figure 2C:
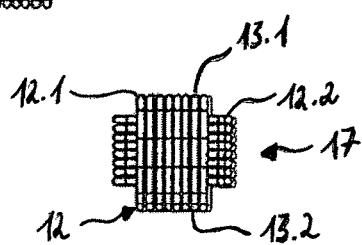
FIG. 2c a schematic plan view of a fiber bundle formed by the two hollow fiber mats shown in FIG. 2b.

In FIG. 2c, a fiber bundle 17 folded from the hollow fiber mats 16 shown in FIG. 2b is shown, where hollow fiber layers 12.1, 12.2 were formed that are rotated with respect to one another by approximately 90 degrees and which protrude from one another with the free ends 13.1, 13.2 of the respective fibers 13. All of the hollow fiber layers 12.1, 12.2 overlap in a (particularly square) core region. Furthermore, there are regions in which only those hollow fiber layers 12.1 or 12.2 overlap where the fibers 13 are oriented in the same direction. In these regions, the fibers 13 of the one layer 12.1 can be processed, in particular opened, at their ends 13.1, 13.2 without the fibers of another layer 12.2 being damaged.

Figure 3A:
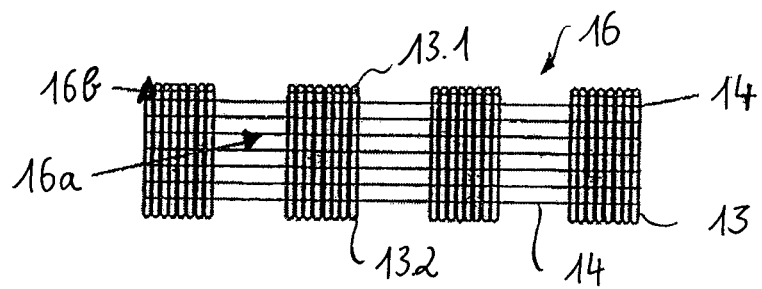
FIG. 3a a schematic plan view of a hollow fiber mat with short fibers that are bundled together into fiber packages which are arranged at a distance to one another, wherein the hollow fiber mat is suited to form a fiber bundle for an oxygenator module according to the invention.

In FIG. 3a, a hollow fiber mat 16 is shown, which is formed from a plurality of hollow fiber packages 16b that are provided at a distance to one another so that empty positions 16b result. Each hollow fiber package 16b has a plurality of fibers 13, in particular up to 200 fibers 13 arranged one next to the other (eight fibers are illustrated by way of an example), wherein the fibers 13 or hollow fiber packages 16b are connected with one another by means of warp threads 14. The warp threads 14 extend orthogonally to the fibers 13 and are longer than the fibers 13.

Figure 3B:
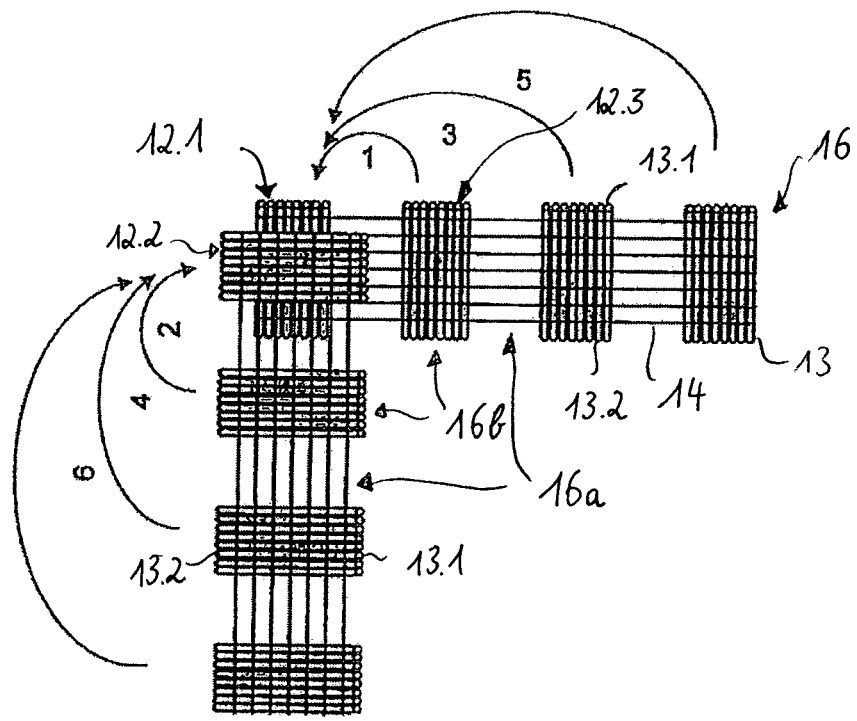
FIG. 3b a schematic plan view of a hollow fiber mat with short fibers which can be folded with another hollow fiber mat with short fibers to form a fiber bundle for an oxygenator module according to the invention.

In FIG. 3b, another hollow fiber mat 16 is shown that is arranged on another hollow fiber mat 16 rotated by 90 degrees with respect to the latter and has the same structure. The two hollow fiber mats 16 can be folded into one fiber bundle by initially folding over the lower hollow fiber mat (arrow 1) and then making additional foldings (arrows 2, 3, 4, 5, and 6). Here, several hollow fiber layers 12.1, 12.2, 12.3 are formed, each of which has fibers 13 that are arranged independently of one another, i.e., are not connected with one another. Here, the free ends 13.1, 13.2 of the fibers 13 can be opened or closed.

Figure 3C:
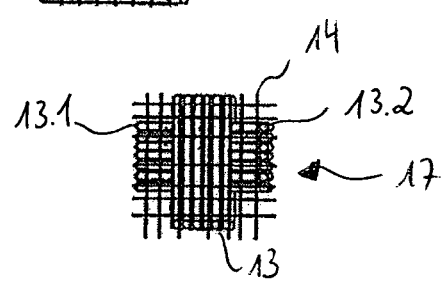
FIG. 3c a schematic plan view of a fiber bundle formed by the two hollow fiber mats shown in FIG. 3b.

In FIG. 3c, a fiber bundle 17 folded from the hollow fiber mats 16 shown in FIG. 3b is shown. The warp threads 14 are provided across a section with square basic shape, i.e., also in regions were no fibers 13 are provided. Here, the warp threads 14 are separated from the fiber bundle 17 after it was folded.

In FIG. 4a, a hollow fiber bundle 17 is shown, which is arranged in a mold 50 to produce a potting. In this mold 50, the hollow fiber bundle 17 can be rotated about a central longitudinal axis M of the hollow fiber bundle, for which it can be arranged on a centrifuge (not shown). Here, the hollow fiber bundle 17 can be fixed in the mold 50 by means of two blood covers or covers (not shown) relative to the mold 50 as long as no potting compound has been introduced into the mold. The individual hollow fiber layers 12 are arranged rotated by 90 degrees with respect to one another and each has a rectangular basic shape with different lateral lengths so that overlapping core regions 12a and protruding, non-overlapping sections 12b are formed. In this way, the free ends 13.1, 13.2 of the fibers 13 of one hollow fiber layer 12 each can be enclosed by potting compound, in particular above and below the hollow fiber layer 12 (with respect to the central longitudinal axis M). This results in a good anchoring or fixing of the fibers in the potting compound and also in good accuracy with regard to the orientation of the fiber ends. Between the individual layers 12, potting compound can be provided in each of the non-overlapping sections 12b.

According to one variant, the hollow fiber layers shown in FIG. 4a can also be arranged at an angle of 45 or 60 degrees to one another, particularly layers laying on top of one another can each be arranged rotated by 45 or 60 degrees to the adjacent layer. In this arrangement of the layers, the surface of the fibers can be utilized even better in comparison to the 90 degree arrangement (orthogonal arrangement).

In FIG. 4b, the hollow fiber bundle 17 is shown in a state of rotation about the axis of rotation D of a centrifuge (here corresponding to the central longitudinal axis M), where potting compound 11 has been introduced into the mold 50. Here, the hollow fiber bundle 17 and/or the mold 50 are fixed on the centrifuge, in particular a rotary disk. Here, the hollow fiber bundle 17 is fixed in the mold 50. Due to a centrifugal force acting on the potting compound 11 as a result of the rotation, the potting compound 11 is driven toward an inner sheath surface of the mold 50 so that the potting compound 11 is given an outer sheath surface 11b, which is a negative of the inner sheath surface of the mold 50. At the same time, an inner sheath surface 11a is formed, the cross section of which is essentially circular as shown and which is at least essentially cylindrical with respect to the central longitudinal axis M. In the case described, an annular potting is created that is at least essentially pipe-like with respect to the central longitudinal axis M and which surrounds an at least essentially cylindrical cavity K. Blood, for example, can flow through this cavity K.

FIG. 5a shows the fiber bundle 17 in a state removed from the mold (not shown), in which the potting compound 11 is solidified and the fiber bundle 17 is already fixed in the potting compound 11. In case polyurethane is used as the potting compound, a curing of the potting compound has already taken place. A circularly potted oxygenator module 10 is provided. The mold can have been removed from the fiber bundle 17 so that the fiber bundle 17 can continue to be arranged or fixed on a rotary disk of a centrifuge.

FIG. 5b shows that the circularly potted oxygenator module 10 can be further processed by means of a cutting device 60 in order to give the outer sheath surface 11b of the potting 11 a certain geometry, for example, or to provide it with a certain structure, roughness or quality. Here, the oxygenator module 10 can continue to be arranged on a centrifuge and the cutting device 60 can be guided toward the rotating oxygenator module 10 like a turning chisel. Here, the cutting(-off) of the fiber ends and/or a lathing of the potting material 11 (in particular by the same cutting process) can also be performed, for example, in order to expose the fiber ends of the fiber bundle 17.

In FIG. 5c, the oxygenator module 10 is shown with a reworked circular potting. The cross section of the outer sheath surface 11b is designed to be circular; the potting itself is designed to be annular or pipe-like along the central longitudinal axis.

In FIG. 6a, a hollow fiber bundle 17 is shown, which is arranged in a mold 50 to produce a potting just like the hollow fiber bundle shown in FIG. 4a. According to one variant, the hollow fiber layers of the hollow fiber bundle 17 shown in FIG. 6a can also be arranged at an angle of 45 or 60 degrees to one another, particularly layers lying on top of one another can each be arranged rotated by 45 or 60 degrees with respect to the adjacent layer.

In FIG. 6b, the hollow fiber bundle 17 is shown in a state of rotation about the axis of rotation D of a centrifuge (here corresponding to the central longitudinal axis M), where both potting compound 11 and a barrier fluid F have been introduced into the mold 50. The barrier fluid F is arranged, during rotation of the mold 50 about the axis of rotation D, outside of the potting compound 11, in particular due to its higher density (relative, volume-specific mass). The barrier fluid F rests against an inner sheath surface of the mold 50.

In FIG. 6c, the barrier fluid was removed after setting of the potting compound 11 in the mold 50 so that a potting is formed which is arranged at a radial distance from the inner sheath surface of the mold 50. The free ends 13.1, 13.2 of the fibers 13 protrude radially outward from the potting. It can be seen that sufficient barrier fluid F was introduced in the process step shown in FIG. 6b so that the potting is arranged radially inward of all free ends 13.1, 13.2. The outer sheath surface 11b of the potting has a smaller diameter than the fibers 13 in their direction of extent. The potting is integrated into the fiber bundle 17 as a thin-walled pipe within the fiber bundle 17, i.e., it is formed by relatively few potting material 11. The potting preferably surrounds a core region, where a first hollow fiber layer 12.1 and a second hollow fiber layer 12.2 completely overlap one another. In other words, the inner sheath surface 11a of the potting 11 preferably has an inner diameter that corresponds to the dimensions of the quadratic core region 12a (shown with diagonal lines). In this way, the potting 11 can also be provided in the four corner regions, where the layers 12.1, 12.2 respectively abut each other with their non-overlapping, protruding sections. Thus, the fiber bundle 17 can, on the one hand, be anchored/fixed in the potting 11 with good stability; on the other hand, it can be avoided that a flow path with particularly low flow resistance is formed in these corner regions (which would be the case if the inner diameter of the potting were larger than the length of the diagonal of the quadratic core region 12a).

In FIG. 7a, an oxygenator 1 is shown, which has an oxygenator module 10 that is fixed in a housing 2 of the oxygenator 1. A potting 11 of the oxygenator module 10 is connected with a cover 20 by means of fasteners 21. The potting 11 has a cylindrical inner sheath surface and with it defines a cylindrical cavity which can be perfused by blood in a homogeneous manner. A blood stream can be distributed onto a hollow fiber bundle 17 by means of an aspect distributor 40 (without swirl elements) or of a swirl distributor 30 with wing-like swirl elements. Another cover (not shown; see cover 20 in FIG. 7b) is arranged between the oxygenator module 10 and the aspect distributor 40. In this way, the blood stream flows through the hollow fiber bundle 17 in a uniform manner. The hollow fiber bundle 17 has a diameter that is larger than a diameter of the aspect distributor 40 or the swirl distributor 30.

In FIG. 7b, the blood stream B is shown in the form in which it can flow through the oxygenator module 10 from a blood inlet 4.1 to a blood outlet 4.2 of the housing 2. Before the blood stream B impinges upon the swirl distributor 30, it is spread by the aspect distributor 40. The swirl distributor 30 has a deflector surface 30b which is arranged below the blood inlet 4.1 and is part of a centrally arranged mandrel or rotationally symmetrical circulation body from which wings 30.1, 30.2 extend radially outward. The swirl distributor 30 laterally directs the blood stream B radially outward, before the blood stream B impinges upon the hollow fiber bundle 17 of the oxygenator module 10. The oxygenator module 10 is coupled by means of the potting 11 with fasteners 21 of the respective cover 20. Upstream of the oxygenator module 10, the respective cover 20 is arranged between the aspect distributor 40 and the potting 11. A blood inlet 4.1 is provided by the aspect distributor 40, and a blood outlet 4.2 is provided by the lower cover 20.

Figure 8:
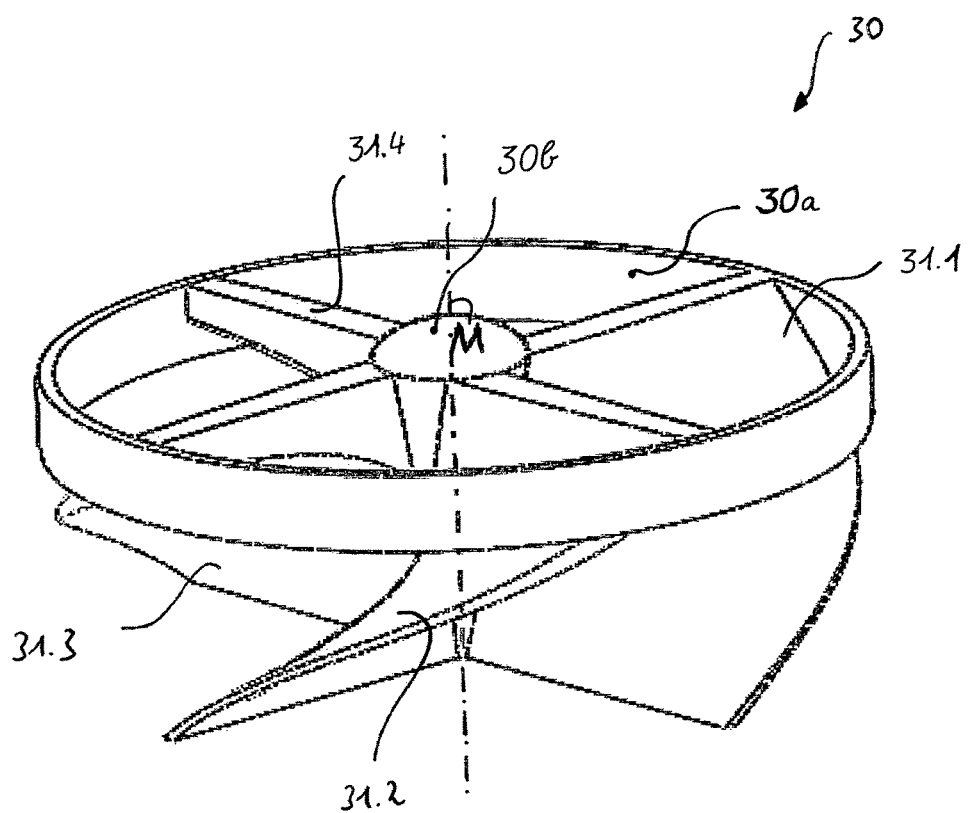
FIG. 8 a schematic perspective view of a swirl distributor for an oxygenator according to one exemplary embodiment of the invention.

In FIG. 8, a swirl distributor 30 is shown which is designed for the (in particular static, rigid, i.e., unmoved) arrangement in an oxygenator according to FIG. 7a, 7b, in particular upstream of an oxygenator module, and which has a deflector surface 30*b* that is concentrically arranged about a central longitudinal axis M and from which four swirl elements or wings 31.1, 31.2, 31.3, 31.4 extend radially outward up to an inner sheath surface 30*a* against which they respectively abut at least approximately orthogonally. The inner sheath surface 30*a* is designed to be at least approximately concentrical about a central longitudinal axis M and has a cross section with a circular geometry. The wings 31.1, 31.2, 31.3, 31.4 merge with one another in the region of the central longitudinal axis M so that the blood stream is separated into different partial flows. Each partial flow can be given a new flow direction which preferably is accompanied by a respective deflection in the range of 90 degrees. In this way, a blood stream can flow through a cavity of an oxygenator module in such a way that a surface as large as possible of hollow fibers arranged in the cavity is circulated, which can ensure an effective gas exchange. By means of the wings 31.1, 31.2, 31.3, 31.4, a blood stream can be deflected particularly strongly. As a result of the uniform design of the wings 31.1, 31.2, 31.3, 31.4, the partial flows can be given a swirl that is largely comparable to the other partial flows so that the partial flows flow through the fibers in the cavity in a uniform manner, in particular with the same angle of inflow and the same flow rate, and also can merge again into one blood stream after a certain distance.

By means of the deflector surface 30*b*, a blood stream can be distributed in a homogeneous manner to four subareas that are defined by the wings. The deflector surface 30*b* has a curvature that is convex against the flow direction which allows for the deflection of the blood stream in a particularly blood-friendly manner.

Figure 9A:
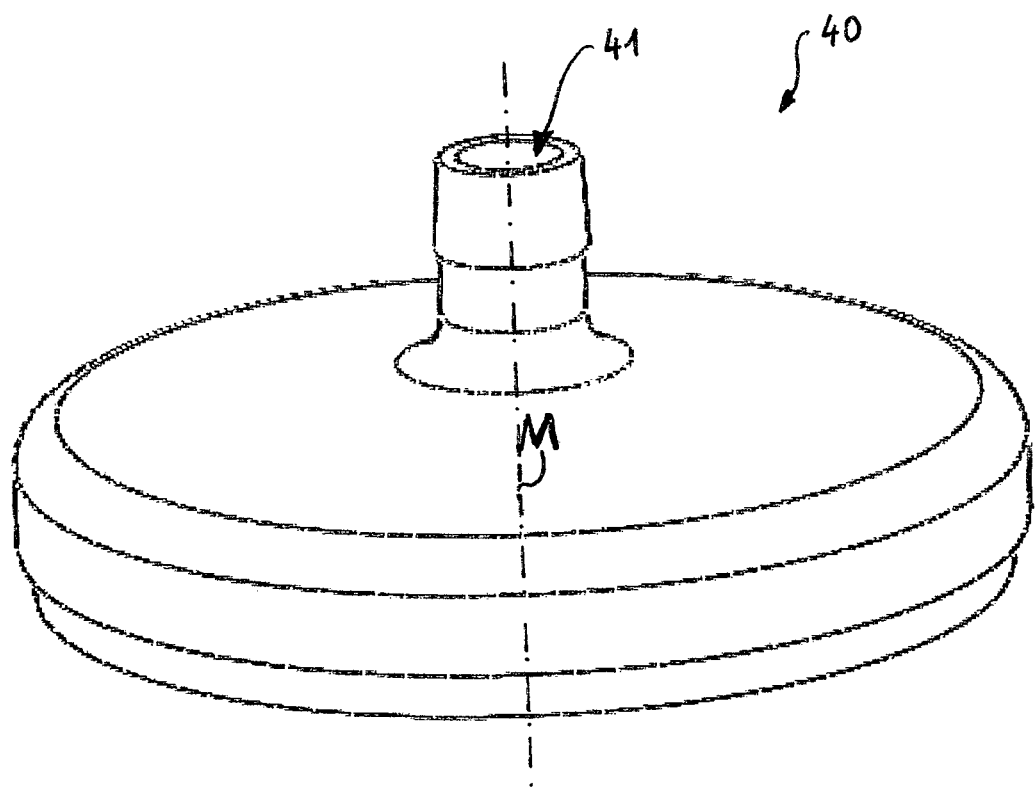
FIG. 9a a schematic perspective view of an aspect distributor for an oxygenator according to one exemplary embodiment of the invention.

In FIG. 9*a*, an aspect distributor 40 is shown, which is designed for the (in particular static, rigid, i.e., unmoved) arrangement in an oxygenator according to FIG. 7, 8*a*, in particular upstream of an oxygenator module, and which has an inner sheath surface 40*a* that is arranged concentrically about a central longitudinal axis M. The aspect distributor 40 has a central orifice 41, through which a blood stream can flow in order to then flow along the inner sheath surface 40*a* and spread with respect to the central longitudinal axis M according to the course of the inner sheath surface 40*a*. The aspect distributor 40 is designed to be rotationally symmetrical about the central longitudinal axis M. The aspect distributor 40 can optionally be used alone or in connection with a swirl distributor.

FIG. 9*b* shows that an inner sheath surface 40*a* of the aspect distributor 40 can have a stepped geometry. The inner sheath surface 40*a* is divided into a, in the flow direction, first inner sheath surface 40*a*.1, a second inner sheath surface 40*a*.2 and a third inner sheath surface 40*a*.3, each of which having a larger radius than the preceding inner sheath surface. In this way, the aspect distributor 40 can be coupled or connected to a cover and a swirl distributor in an appropriate manner as shown in FIG. 8*b*. The swirl distributor can centrally abut against the second inner sheath surface 40*a*.2, and the aspect distributor 40 itself can be centered with respect to the cover by means of the third inner sheath surface 40*a*.3. Here, a blood stream only comes into contact with the first inner sheath surface 40*a*.1. The aspect distributor 40 shown in FIG. 10*b* can optionally also be provided with one or several swirl elements and be developed into a swirl distributor.

FIG. 10 shows a tangential distributor 45, which has an orifice 46 and a tangential inlet 47 as well as an inner sheath surface 45*a* that is arranged concentrically about a central longitudinal axis M. The tangential distributor 45 has no swirl elements. The inner sheath surface 45*a* is divided into a, in the flow direction, first inner sheath surface 45*a*.1, a second inner sheath surface 45*a*.2 and a third inner sheath surface 45*a*.3, with the first inner sheath surface 45*a*.1 and the second inner sheath surface 45*a*.2 preferably having the same radius. The inlet 47 opens at the second inner sheath surface 45*a*.2 and thus in the area of a swirl distributor, for example, with which the tangential distributor 45 can optionally be coupled. In this way, the deflection of the blood stream can take place in a more effective manner. By means of the tangential inflow and the associated rotation of the blood stream, it can be avoided that air bubbles form that cannot escape. In case that air bubbles occur anyway, they can collect in the center of the distributor and escape in particular in the direction of the orifice 46. Here, a supply blood stream can optionally be guided in part through the orifice 46, which preferably is designed to be smaller in comparison to the orifice of an aspect distributor.

Figure 11:
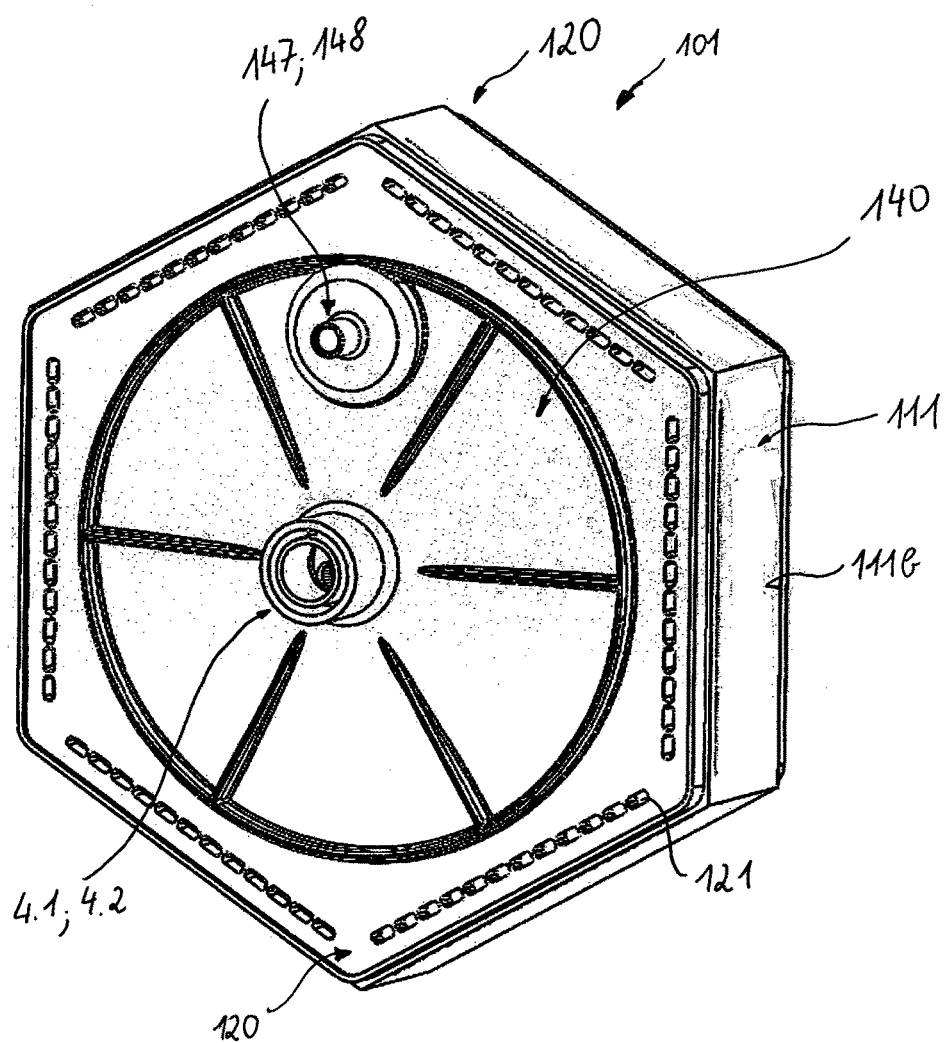
FIG. 11 a schematic perspective view of a hexagonal oxygenator with a (hexagonal) cover according to another exemplary embodiment of the invention.

FIG. 11 shows an oxygenator 101, which has a hexagonal potting 111. The potting 111 has an outer sheath surface 111*b* with six, at least approximately flat, even surface sections. The hexagonal outer geometry of the potting 111 can particularly be manufactured by cutting.

Furthermore, a cover 120 is shown, which is connected with the potting 111. The cover 120 has a hexagonal geometry with six equilateral outer sheath surface sections. On the cover 120 are arranged fasteners 121, by means of which the cover 120 can be connected with the potting 111 (the set/setting potting compound). The fasteners 121 can be designed as snap-in noses, protruding shoulders or edges and/or as recesses. The fasteners 121 can be embedded into the potting 111 during casting of the potting compound. The fasteners 121 respectively extends lengthwise along each outer sheath surface section. Below the potting 111, another cover 120 is provided. At least one oxygenator module (not shown) is arranged between the covers 120.

In the cover 120, a distributor or distributor section 140 is formed. The distributor 140 is preferably formed by the cover 120 and can have radially oriented reinforcement bars. The cover 120 can optionally also have an opening or receptacle that geometrically corresponds to the distributor 140 and in which a separate distributor can be arranged. On the distributor 140 is provided a centrally arranged blood inlet 4.1 or blood outlet 4.2. The distributor 140 also has a laterally arranged inlet 147 or outlet 148, in particular a vent, which is arranged at the uppermost point of the oxygenator 101.

Figure 12A:
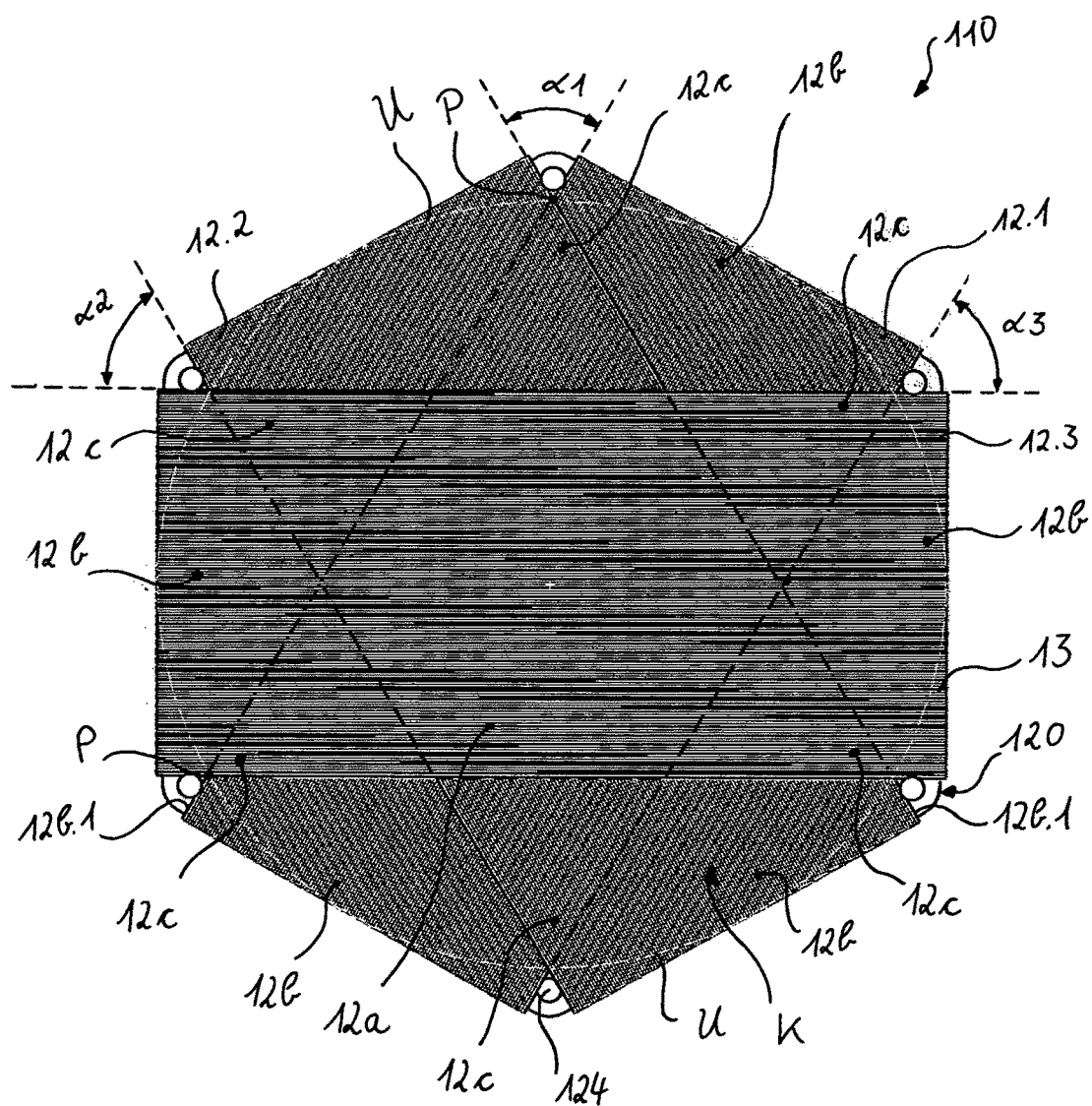
FIG. 12A, 12B each a schematic plan view of components of an oxygenator module according to another exemplary embodiment of the invention in an arrangement on a cover.

FIG. 12A shows an oxygenator module 110 or at least components thereof, which can be used in connection with the cover 120 shown in FIG. 11 and the distributor 140. The oxygenator module 110 has a plurality of individual hollow fiber layers of which a first hollow fiber layer 12.1, a second hollow fiber layer 12.2 and a third hollow fiber layer 12.3 are illustrated here by way of example. Each hollow fiber layer has a plurality of fibers 13 oriented linearly in one direction. Here, the first hollow fiber layer 12.1 is arranged at the bottom. The second hollow fiber layer 12.2 is arranged on top of the first hollow fiber layer 12.1, and the third hollow fiber layer 12.3 is arranged on top of the second hollow fiber layer 12.2. The respective hollow fiber layers are arranged rotated at an angle to one another. The first hollow fiber layer 12.1 is arranged at an angle of rotation $\alpha 1$ with respect to the second hollow fiber layer 12.2. The second hollow fiber layer 12.2 is arranged at an angle of rotation $\alpha 2$ with respect to the third hollow fiber layer 12.3. The third hollow fiber layer 12.3 is arranged at an angle of rotation $\alpha 3$ with respect to the first hollow fiber layer 12.1. Preferably, the angles of rotation are each at least approximately 60 degrees. Preferably, the angles of rotation are exactly the same size. With angles of rotation of exactly 60 degrees, the same relative arrangement of additional layers can be ensured after three layers each so that each of the layers can be flown about in the same way.

The hollow fiber layers are arranged on a hexagonal cover 120, on each corner of which an orientation element 124, in particular a centering pin, is arranged, by means of which the layers 12.1, 12.2, 12.3 can be positioned relative to the cover 120. Here, the orientation element 124 can also be used for the relative positioning of the opposite covers 120 at a predefined distance to one another, in particular during casting, i.e., when forming the potting. Here, the orientation element 124 can also fulfill the function of a spacer.

With respect to the three layers 12.1, 12.2, 12.3, the arrangement staggered by 60 degrees respectively results in three different regions or sections. In a core region 12a, all three layers overlap one another. The core region 12a has a hexagonal basic shape. In a respective, protruding region or section 12b, none of the three layers overlaps the other two layers. In total, six of these non-overlapping, exposed sections 12b are formed. The non-overlapping, exposed sections 12b each have a triangular geometry with a rectangular section that is radially outward directly adjacent to it. Furthermore, partially overlapping sections 12c are also formed, in which two of the three layers overlap one another. The partially overlapping sections 12c have a triangular geometry.

The non-overlapping, exposed sections 12b each have exposed lateral edge sections 12b.1, by means of which a respective layer abuts against the respective orientation element 124. The oxygenator module 110 or the three layers 12.1, 12.2, 12.3 and the cover 120 are at least approximately designed to be superposable. In a plan view, the three layers 12.1, 12.2, 12.3 and the cover 120 at least approximately take up the same base area. Here, the length of the layers after a processing step, in particular after a cutting, is shown. Prior to the processing step, the lengths can be longer.

In FIG. 12A, a circumferential line U is also indicated, which marks an outer sheath surface of a potting (not shown), in particular a minimum diameter of the outer sheath surface. The circumferential line U or the potting surrounds a cavity K, in which the hollow fiber layers 12.1, 12.2, 12.3 are essentially arranged and which can be perfused by a fluid. In manufacturing the oxygenator module 110, a barrier fluid can be used, which is driven outward as a result of a centrifugal force. The amount of the barrier fluid can define the position of the outer sheath surface of the potting. The circumferential line U is circular, with the diameter of the circumferential line U corresponding at least approximately to the distance of opposite fiber ends. Preferably, the diameter is at most as large as the distance, more preferably slightly smaller than the distance so that all fiber ends protrude from the potting and are exposed. By the diameter preferably being (almost) equal to the distance, the fiber material can be used particularly effectively. According to one variant (as shown), the circumferential line U intersects the respective lateral edge of a respective layer at a point P where the lateral edges of adjacent layers also intersect. By means of this arrangement of the potting, a particularly advantageous compromise in utilizing the available volume and the usable fiber surface can be ensured, especially in connection with the arrangement of the layers rotated by 60 degrees.

Figure 12B:
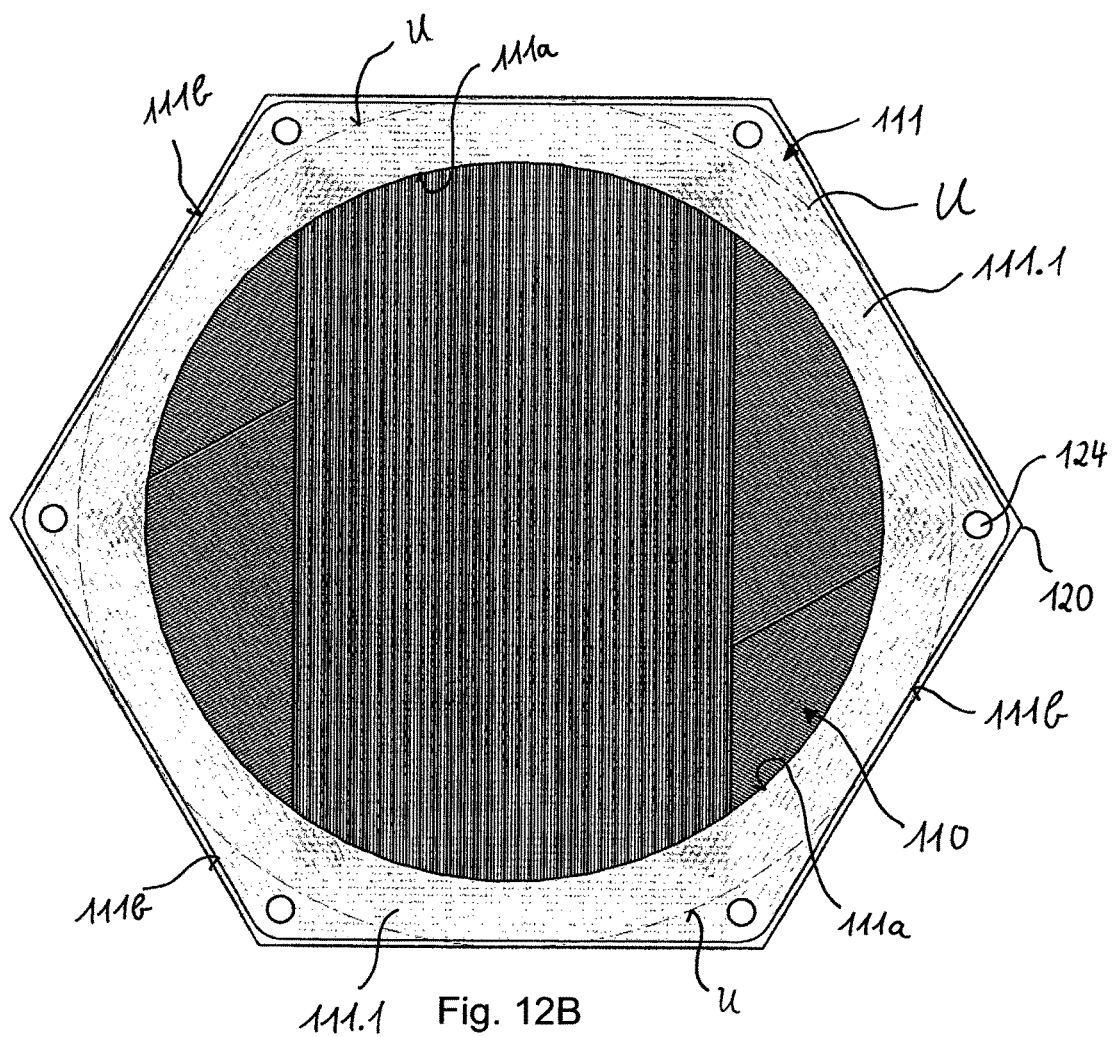

FIG. 12B essentially shows the same components as FIG. 12A. In addition, the potting 111 is shown, from which orientation elements 124 protrude. The potting 111 is arranged on a cover 120. The potting 111 has an annular section 111.1, in which the oxygenator module 110 is embedded. The annular section 111.1 is limited on the inside by the inner sheath surface 111a of the potting and on the outside by the circumferential line U. The potting 111 has an outer sheath surface 111b, the cross section of which has a hexagonal geometry. It can be seen that the potting 111 is only used for embedding the fiber layers in a comparably small region, namely in a region respectively radially outside of the orientation elements 124.

Figure 13A:
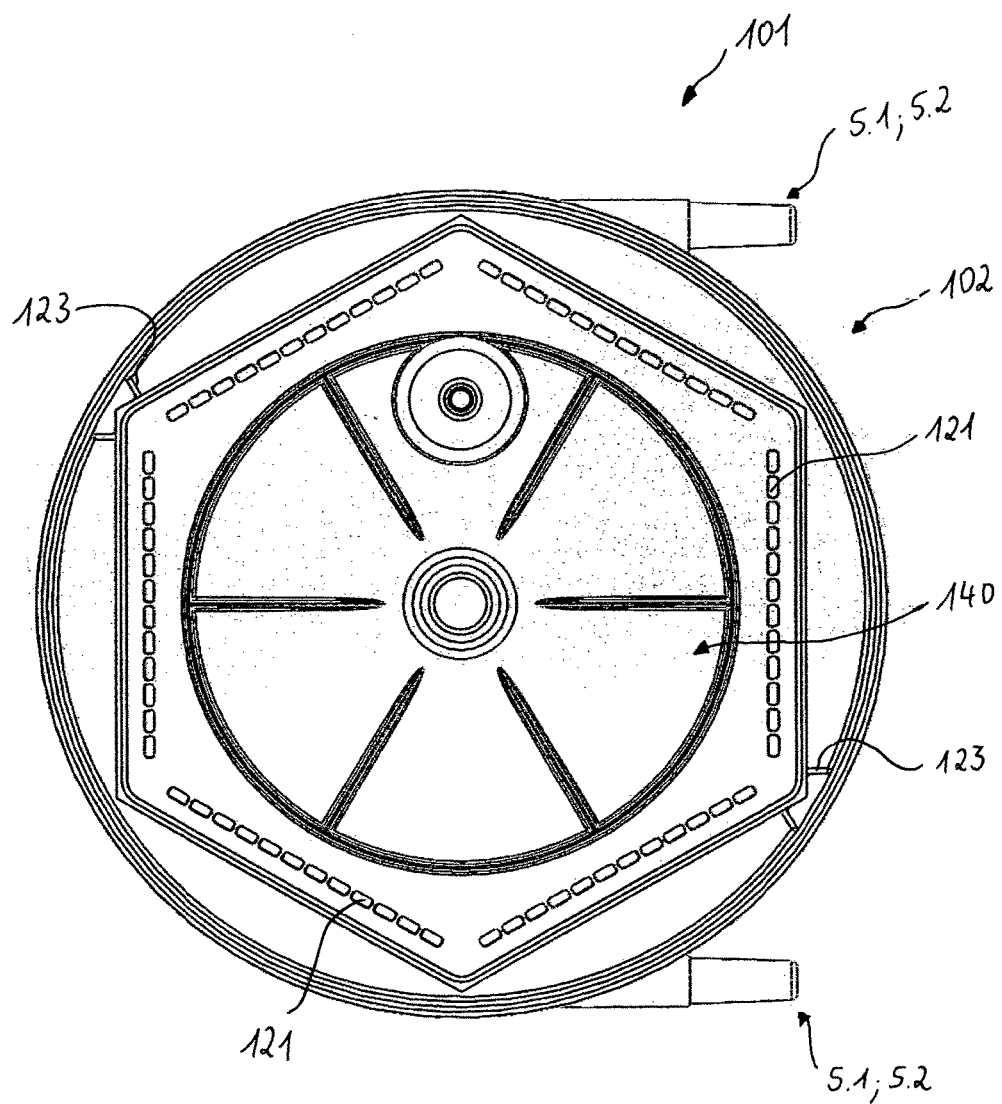
FIG. 13A, 13B a schematic plan view and a perspective view of an oxygenator according to one exemplary embodiment of the invention with the hexagonal cover shown in FIG. 11 in an arrangement in a housing of the oxygenator.

FIG. 13A shows an oxygenator 101 with an (outer) housing 102, which has an additional fluid inlet 5.1 (in particular gas inlet) and an additional fluid outlet 5.2 (in particular gas outlet). A cover 120, for example the cover shown in FIG. 11, is arranged in the housing 102 and supported by an inner sheath surface of the housing by means of fasteners 123. Here, an oxygenator module arranged in the oxygenator 101 can be inserted into the outer housing 102 with two covers and be supported. Furthermore, an additional cover (not shown) can be provided, which seals the outer housing 102 in an air-tight manner.

Figure 13B:
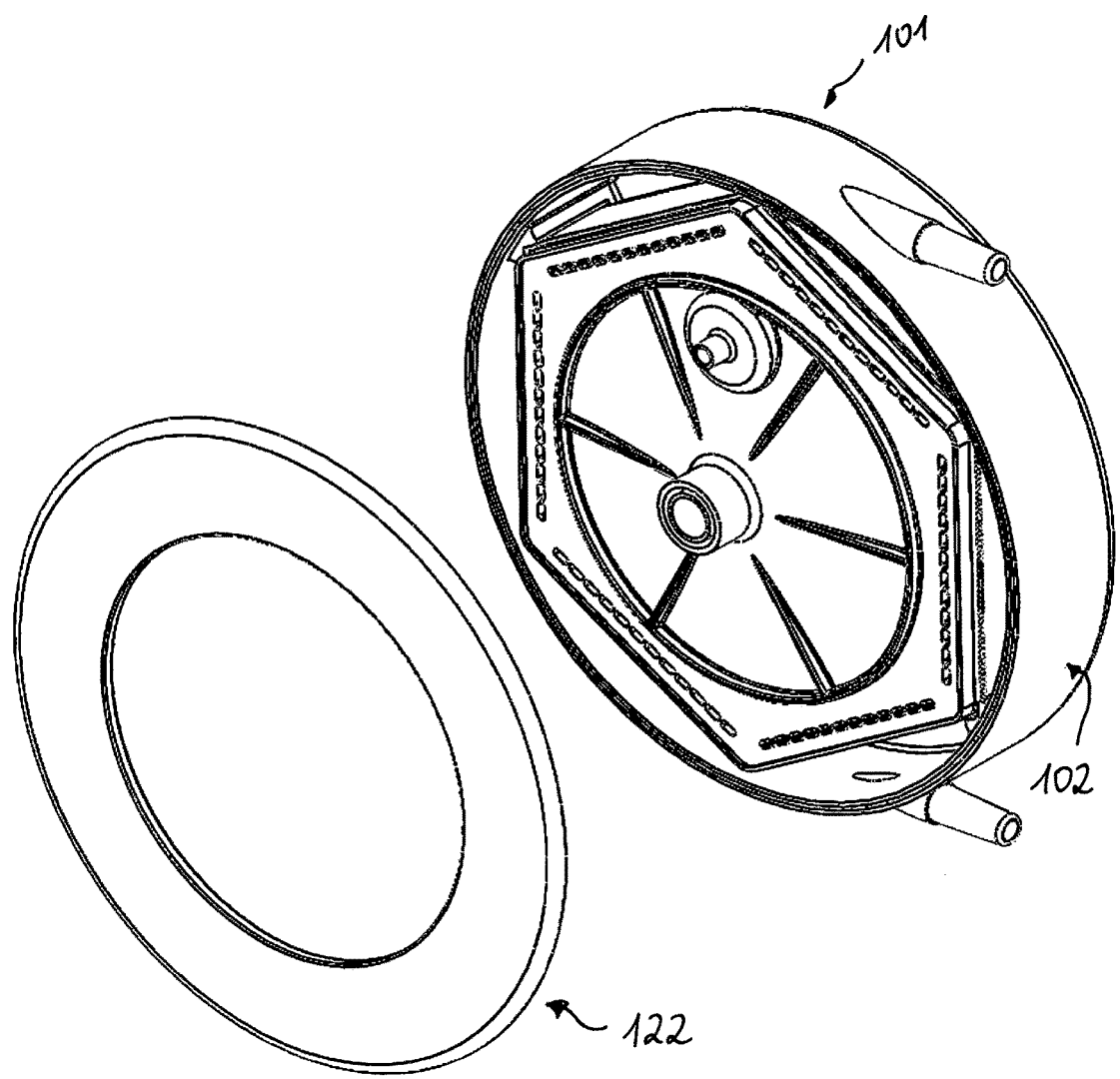

FIG. 13B shows an additional cover 122 for covering the (outer) housing 102. The cover 122 has the form of a disk-shaped ring.

Figure 14:
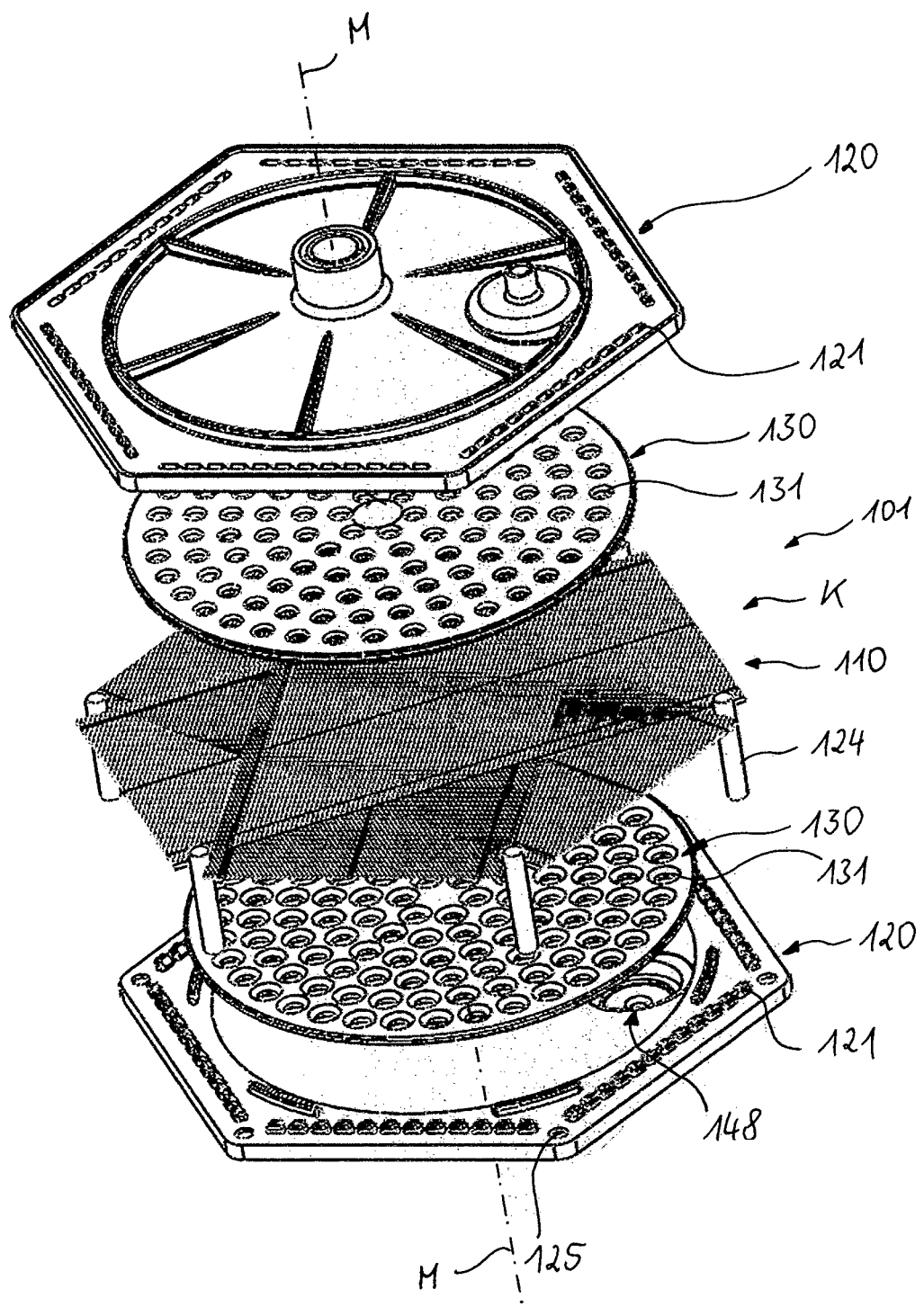
FIG. 14 a schematic perspective exploded view of individual components of an oxygenator according to one exemplary embodiment of the invention, particularly also with the cover shown in FIG. 11 and the components of the oxygenator module shown in FIG. 12A, 12B.

FIG. 14 shows an oxygenator 101 with two hexagonal covers 120, orientation elements 124, a hexagonal oxygenator module 110 as well as two circular distribution elements 130 (blood distributor plate which is designed to geometrically correspond to the cavity). The cover 120 could be constructed identically, which increases the symmetry of the arrangement and can reduce the number of components. In the assembled state, the cover 120 is surrounded by a cavity K which extends along the indicated central longitudinal axis M of the oxygenator 101 or the oxygenator module 110. The lower cover 120 has an outlet 148 or a rear vent. Furthermore, an invisible, centrally arranged blood outlet is provided. The cover 121 has recesses 125 to accommodate a respective orientation element 124. The two distribution elements 130 are arranged on both sides of the oxygenator module 110. Optionally, only a single distribution element 130 can also be provided, in particular on the upstream side. Each distribution element 130 has a plurality of holes or passages 131 which are arranged at least approximately uniformly distributed on the distribution element 130. As shown, the passages 131 can be arranged on different partial circles concentrically to a central point of the distribution element 130. All passages 131 have at least approximately the same distance to one another. The distribution elements 130 are designed to be disk-like. By means of the respective distribution element 130, a fluid stream can be spread areally across the entire cross sectional area of the cavity K.

REFERENCE SYMBOL LIST

1; 101 Oxygenator
2; 102 Housing
4.1 Blood inlet
4.2 Blood outlet
5.1 (Additional) fluid inlet, in particular gas inlet
5.2 (Additional) fluid outlet, in particular gas outlet
10; 110 Oxygenator module
10' Oxygenator module according to the prior art
11; 111 Potting or potting compound
111.1 Annular section
11' Potting in an oxygenator module according to the prior art
11a; 111a Inner sheath surface of the potting 11b; 111b Outer sheath surface of the potting
12 Hollow fiber layer
12.1 First hollow fiber layer
12.2 Second hollow fiber layer
12.3 Third hollow fiber layer
12a Overlapping core region
12b Protruding, non-overlapping section
12b.1 Exposed lateral edge section
12c Partially overlapping section
13 Hollow fiber
13.1 (First) free end of a hollow fiber
13.2 (Second) free end of a hollow fiber
14 Warp thread
16 Hollow fiber mat
16a Empty position
16b Hollow fiber package
17 Hollow fiber bundle
17' Hollow fiber bundle in an oxygenator module according to the prior art
20; 120 Cover
21; 121 Fastener on the cover
122 Additional cover to cover the (outer) housing
123 Fastener between cover and housing
124 Spacer or orientation element, in particular centering pin
125 Recess to accommodate the orientation element
30 Swirl distributor 30a Inner sheath surface
130 Distribution element, in particular distributor plate
131 Hole or passage
30b Deflector surface
31.1 (First) swirl element
31.2 (Second) swirl element
31.3 (Third) swirl element
31.4 (Fourth) swirl element
40 Aspect distributor
140 Distributor or distributor section on the cover
40a Inner sheath surface
40a.1 Third inner sheath surface
40a.2 Third inner sheath surface
40a.3 Third inner sheath surface
41 Orifice
45 Tangential distributor
45a Inner sheath surface
46 Orifice
47 Tangential inlet
147 Lateral inlet, in particular vent
148 Lateral inlet, in particular vent
50 Mold, in particular female mold
50' Mold for an oxygenator module according to the prior art
60 Cutting device
B Blood or blood stream
D Axis of rotation
F Barrier fluid
K Cavity
M Central longitudinal axis
P Intersection point between circumferential line and lateral edge of a layer
U Circumferential line
α1 Angle of rotation about the central longitudinal axis between the first and second layer
α2 Angle of rotation about the central longitudinal axis between the second and third layer
α2 Angle of rotation about the central longitudinal axis between the third and first layer The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An oxygenator for gas exchange between blood and a gas in an extracorporeal lung support system, the oxygenator comprising:
at least one oxygenator module including:
several layers of semipermeable, gas-perfusable hollow fibers, with the hollow fibers of one of the layers being oriented at an angle of rotation about a central longitudinal axis of the at least one oxygenator module with respect to the hollow fibers of another one of the layers;
a potting, which extends along the central longitudinal axis and in which hollow fibers are fixed, wherein the potting defines a cavity that extends along the central longitudinal axis and in which hollow fibers are arranged and which is blood-perfusable in a direction of the central longitudinal axis, the potting having a circular inner sheath surface which limits the cavity radially outward;
a blood inlet and a blood outlet, respectively, positioned within the cavity of the at least one oxygenator module;
a housing to accommodate the at least one oxygenator module, wherein the housing has a gas inlet and a gas outlet, each of the gas inlet and the gas outlet is coupled to the hollow fibers of the at least one oxygenator module; and
a distributor device having a central axis that is coincident with the central longitudinal axis of the at least one oxygenator module through which the cavity extends, the distributor device being arranged, with respect to the central longitudinal axis of the at least one oxygenator module, upstream of the at least one oxygenator module and downstream of the blood inlet, the distributor device having a peripheral body that is sized and shaped to allow fluid flowing from the blood inlet to internally flow through the distributor device, wherein the oxygenator is set up for a central inflow of the at least one oxygenator module.

2. The oxygenator according to claim 1, wherein the layers of the at least one oxygenator module are arranged partially overlapping each other.

3. The oxygenator according to claim 1, wherein the potting of the at least one oxygenator module includes a cylindrical outer sheath surface from which the hollow fibers radially protrude with at least one free end.

4. The oxygenator according to claim 1, wherein the at least one oxygenator module has an outer geometry with more than four corners to form either a hexagonal outer profile or an octagonal outer profile.

5. The oxygenator according to claim 1, wherein at least two of the layers are arranged rotated relative to one another at an angle greater than zero and less than 90 degrees, the layers being rotated about the central longitudinal axis.

6. The oxygenator according to claim 1, wherein the layers of the at least one oxygenator module have a rectangular basic shape with different lateral lengths.

7. The oxygenator according to claim 1, wherein the blood inlet and the blood outlet are arranged centrally with respect to the at least one oxygenator module.

8. The oxygenator according to claim 1, wherein the distributor device comprises a swirl distributor having the peripheral body, the swirl distributor is configured to guide a blood stream internally through the swirl distributor with a swirl at a flow angle to the central longitudinal axis and into the cavity, the peripheral body of the swirl distributor having an inner sheath surface with a circular cross section and internal swirl elements that merge into one another toward a central point of the swirl distributor.

9. The oxygenator according to claim 1, wherein the oxygenator further comprises:
at least one cover which is fixed by the potting of the oxygenator module and which has a hexagonal outer geometry.

10. The oxygenator according to claim 1, further comprising at least one of an aspect distributor or a tangential distributor.

11. The oxygenator according to claim 1, wherein the distributor device comprises a swirl distributor having the peripheral body, the swirl distributor including internal swirl elements in the form of four wings.

12. The oxygenator according to claim 1, wherein the angle of rotation about the central longitudinal axis at which the hollow fibers of one of the layers are oriented with respect to the hollow fibers of another one of the layers is between 45 degrees and 90 degrees.

13. A method for producing an oxygenator module for an oxygenator of an extracorporeal lung support system, the method comprising:
arranging a majority of hollow fiber layers within a mold, where the hollow fibers of a first one of the layers are oriented at an angle of rotation about a central longitudinal axis of the oxygenator module with respect to the hollow fibers of a second one of the layers, the angle of rotation of hollow fibers of the first one of the layers with respect to hollow fibers of the second one of the layers being between 45 degrees and 90 degrees;
arranging the mold with respect to an axis of rotation of a centrifuge, the arranging the mold positioning the axis of rotation within the mold;
feeding potting compound into the mold;
while feeding potting compound into the mold, rotating the mold about the axis of rotation in order to exert a centrifugal force on the potting compound in order to arrange the potting compound radially outward in the mold, the rotating forming a cavity that defines a circular inner sheath surface of the potting compound;
curing the potting compound in order to fix the hollow fiber layers via continuous rotation;
removing the potting compound together with the hollow fiber layers from the mold or at least from a part of the mold.

14. The method according to claim 13 comprising embedding the layers in the potting compound, such that the layers are arranged partially overlapping each other.

15. The method according to claim 13 comprising arranging at least one cover in the mold, the arranging the at least one cover causing the potting compound to fix the at least one cover in order to delimit the cavity.

16. The method according to claim 13 comprising:
arranging a barrier fluid that has a higher density than the potting compound on an inner sheath surface of the mold prior to the feeding the potting compound into the mold; and
draining the barrier fluid after the curing the potting compound and prior to the removing the potting compound.

17. The method according to claim 13 wherein hollow fibers of a third one of the layers are rotated about the central longitudinal axis with respect to the hollow fibers of the first one or the second one of the layers at the angle of rotation between 45 degrees and 90 degrees.

* * * * *